United States Patent
Chung et al.

(10) Patent No.: US 10,017,733 B2
(45) Date of Patent: Jul. 10, 2018

(54) PRODUCTION OF PARTHENOGENETIC STEM CELLS AND PATIENT-SPECIFIC HUMAN EMBRYONIC STEM CELLS USING SOMATIC CELL NUCLEAR TRANSFER

(71) Applicant: Sung Kwang Medical Foundation, Seoul (KR)

(72) Inventors: Young Gie Chung, Shrewsbury, MA (US); Dong Ryul Lee, Seoul (KR)

(73) Assignee: Sung Kwang Medical Foundation, Seoul (KR)

( * ) Notice: Subject to any disclaimer, the term of this patent is extended or adjusted under 35 U.S.C. 154(b) by 0 days.

(21) Appl. No.: 14/180,825

(22) Filed: Feb. 14, 2014

(65) Prior Publication Data

US 2014/0234968 A1 Aug. 21, 2014

Related U.S. Application Data

(60) Provisional application No. 61/765,548, filed on Feb. 15, 2013, provisional application No. 61/765,563, filed on Feb. 15, 2013.

(51) Int. Cl.
*C12N 5/0735* (2010.01)

(52) U.S. Cl.
CPC ........ *C12N 5/0606* (2013.01); *C12N 2501/60* (2013.01); *C12N 2517/10* (2013.01)

(58) Field of Classification Search
CPC .................................................. C12N 5/0607
See application file for complete search history.

(56) References Cited

U.S. PATENT DOCUMENTS

| | | |
|---|---|---|
| 2004/0091936 A1 | 5/2004 | West |
| 2008/0299091 A1 | 12/2008 | Revazova et al. |
| 2012/0083032 A1 | 4/2012 | Roh et al. |
| 2012/0184466 A1 | 7/2012 | Revazova et al. |

FOREIGN PATENT DOCUMENTS

| | | |
|---|---|---|
| CN | 1922307 A | 2/2007 |
| CN | 101525592 A | 9/2009 |
| CN | 101535468 A | 9/2009 |
| JP | 2005510232 A | 4/2005 |
| JP | 2007516720 A | 6/2007 |
| JP | 2009512450 A | 3/2009 |
| WO | 03/046141 A2 | 6/2003 |
| WO | 03/100018 A2 | 12/2003 |
| WO | 2007047979 A2 | 4/2007 |
| WO | 2008013557 A1 | 1/2008 |
| WO | 2008124142 A1 | 10/2008 |
| WO | 2009015036 A1 | 1/2009 |
| WO | 2010134076 A1 | 11/2010 |
| WO | 2012/029957 A1 | 3/2012 |
| WO | 2014125363 A1 | 8/2014 |

OTHER PUBLICATIONS

Tachibana, Cell, Jun. 2013, 153:1228-1238.*
Noggle, Nature, 2011, 478:70-75.*
Chung (2014, Cell Stem Cell, 14:777-780).*
Takahashi (2007, Cell, 131:861-872).*
Nasr-Esfahani (2010, Fertility and Sterility, 94:520-526).*
International Search Report and Written Opinion dated Jun. 25, 2014 (Jun. 25, 2014) for International application No. PCT/IB2014/000160.
Qiang Wu, et al., "CARM1 is Required in Embryonic Stem Cells to Maintain Pluripotency and Resist Differentiation," Stem Cells, 2009, pp. 2637-2645, vol. 27, No. 11.
International Preliminary Report on Patentability dated Aug. 27, 2015 (Aug. 27, 2015) for International application No. PCT/IB2014/000160.
Matsuura et al. P34cdc2 Kinase and MAP Kinase Activities and Parthenogenetic Activation in Porcine Oocytes after Injection of Miniature Pig Sperm Extracts. J Mamm Ova Res (2008). 25:63-68.
Okada et al. Activation and Development of Pig Oocytes after Microinjection of Crude Sperm Extract. J Mamm Ova Res (2004). 21:134-140.
Torres-Padilla et al. Histone arginine methylation regulates pluripotency in the early mouse embryo. Nature (2007). 445(7124):214-218.
Chen et al., Progress in the Studies of Parthenogenetic Embryonic Stem Cells, 2004, National Journal of Andrology, vol. 1(1), pp. 55-58.
Fan et al, Derivation of Cloned Human Blastocysts by Histone Deacetylase Inhibitor Treatment after Somatic Cell Nuclear Transfer with β-Thaassemia Fibroblasts, Stem Cells and Development, 2011, vol. 20(11), pp. 1951-1959.
EP 147512933 Extended Search Report dated Aug. 16, 2016; 9 pages.
Byrne et al. Producing Primate Embryonic Stem Cells by Somatic Cell Nuclear Transfer. Nature(2007). 450:497-502.
Chung et al. Human Somatic Cell Nuclear Transfer Using Adult Cells. Cell Stem Cells (2014). 14:1-4.
Ju et al. Establishment of Stem Cell Lines from Nuclear Transferred and Parthenogenetically Activated Mouse Oocytes for Therapeutic Cloning. Fertility and Sterility (2008). 89(Supp13):1314-1323.
Rideout et al. Correction of a Genetic Defect by Nuclear Transplantation and Combined Cell and Gene Therapy. Cell (2002). 109:17-27.

(Continued)

*Primary Examiner* — Valarie E Bertoglio
(74) *Attorney, Agent, or Firm* — Stephen W. Chen; Nixon Peabody LLP

(57) ABSTRACT

Immunocompatible pluripotent stem cells (pSCs), which include cells compatible with different patient populations or patient-specific cells, find wide application in regenerative medicine therapies. Described herein are immunocompatible pSCs generated using techniques such as parthenogenesis resulting in cells possessing desired haplotypes of reduced zygosity, antigenically compatible with multiple patient populations, or nuclear transfer allowing generation of patient-specific cells. Methods described herein related to parthenogenesis, nuclear transfer, or pSC cell line generation. Also described herein are compositions of immunocompatible pSCs and cell lines generated by the aforementioned techniques.

6 Claims, 2 Drawing Sheets

(56) References Cited

OTHER PUBLICATIONS

Tachibana et al. Human Embryonic Stem Cells Derived by Somatic Cell Nuclear Transfer. Cell (2013). 153:1-11.
Wakayama et al. Differentiation of Embryonic Stem Cell Lines Generated from Adult Somatic Cells by Nuclear Transfer. Science (2001). 292:740-743.
Wang et al. Caffeine can be used for Oocyte Enucleation. Cellular Reprogramming (2011). 13(3):225-232.
Mai, Q. et al., Derivation of human embryonic stem cell lines from parthenogenetic blastocysts. Cell Research (2007) 17:1008-1019.
Rybouchkin et al., Role of histone acetylation in reprogramming of somatic nuclei following nuclear transfer. Biology of Reproduction, 2006, vol. 74, pp. 1083-1089.
Kishigami et al., Significant improvement of mouse cloning technique by treatment with trichostatin A after somatic nuclear transfer. Biomedical and Biophysical Research Communication, 2006, vol. 340, pp. 183-189.
Liu W et al, Genetic and epigenetic X-chromosome variations in a parthenogenetic human embryonic stem cell line. Journal of Assisted Reproduction and Genetics, 2011, 28(4):303-313.
Xu Ping, Analysis of International Development Trend of Stem Cell Research, International Development of Stem Cells, Science Focus, vol. 6, No. 2, 2011 (Abstract only).
Wu et al., CARM1 is required in embryonic stem cells to maintain pluripotency and resist differentiation. Stem Cells, 2009,vol. 27(11):2637-2645.

\* cited by examiner

PRODUCTION OF PARTHENOGENETIC STEM CELLS AND PATIENT-SPECIFIC HUMAN EMBRYONIC STEM CELLS USING SOMATIC CELL NUCLEAR TRANSFER

CROSS-REFERENCE TO OTHER APPLICATIONS

This application includes a claim of priority under 35 U.S.C. § 119(e) to U.S. provisional patent applications No. 61/765,548, and 61/765,563, each filed Feb. 15, 2013.

FIELD OF THE INVENTION

The invention relates to immunocompatible pluripotent stem cells (pSCs), including patient-specific pSCs. Methods described herein related to parthenogenesis or nuclear transfer and compositions of immunocompatible pSCs generated by these techniques find wide application in regenerative medicine therapies.

BACKGROUND

Human pluripotent stem cells (hPSCs), possess the remarkable ability to differentiate into virtually all somatic cell types in the body (pluripotency), while maintaining proliferative capacity in an undifferentiated state (self-renewal). These unique features of hPSCs provides opportunity to generate transplantable cells and tissue material for treatment of diseases and conditions ranging from diabetes, osteoarthritis, and Parkinson's disease, among many others. As many human injuries and diseases result from cellular defects, including those of a single cell type, replacement with appropriate stem cells, progenitor cells, or in vitro differentiated cells, could lead to novel therapeutic approaches in the clinic. Moreover, whereas live donors, cadaveric or fetal sources have served as sources of transplant material, the self-renewal capacity of pluripotent stem cells further provides a near limitless resource of transplantable material. An additional benefit is that hPSCs can be generated in a patient-specific manner, thereby leading to therapauetic approaches that reduce risk of immunological rejection and tolerance. Thus, there is considerable enthusiasm for regenerative cell transplantation, including immunocompatible hPSCS and patient-specific hPSCs.

One strategy for generation of immunocompatible hPSCs is to facilitate parthenogenesis (i.e., asexual reproduction) from an oocyte to generate blastocysts for hPSC isolation. Briefly, this approach relies on artificially inducing oocytes to undergo meiotic and mitotic processes in the absence of sperm fertilization, leading to a diploid (2 maternal genome) parthenote, which can be cultured further into blastocyst from which hPSCs can be isolated. Using the parthenogenesis approach, the isolated hPSCs are known as parthenote-derived human pluripotent stem cells (pn-hPSCs).

An alternative approach allows for generation of patient-specific hPSCs through somatic cell nuclear transfer (SCNT). Somatic cell nuclear transfer involves isolation of the nucleus of a somatic cell of a donor patient and insertion into an enucleated recipient oocyte. Transfer of the donor nucleus to the recipient oocyte's cytoplasm results in reprogramming of the transferred donor nucleus through silencing of somatic cell genes and activation of embryonic genes. From reconstructed oocytes, one can establish blastocysts in culture to isolate hPSCs from the inner cell mass (ICM). As the result of nuclear transfer the hPSCs (NT-hPSCs) carry the nuclear genetic material of the patient, which are patient-specific. There is significant overlap in technical procedures related both techniques. For example, early attempts to achieve NT-hPSC cell lines resulted in the accidental and first known instance of pn-hPSC cell line generation.

Despite promising advances in parthenogenesis and SCNT techniques, there are significant limitations that, at present, preclude practical clinical application. For example, existing parthenogenesis studies have reported successful oocyte activation in approximately 50% of donor oocytes, but a key limitation appears to be induction of blastocyst formation, which can dip to as low as 15% or less of activated oocytes. As related to nuclear transfer, using conventional techniques, only up to as few as 2% of reconstructed oocytes cross the 8-cell threshold towards blastocyst formation. Together, these limitations can mean less than 10% of donor oocytes are successfully cultivated into pn-hPSCs. Subsequent pn-hPSCs may suffer from other undesirable attributes such as aneuploidy or karyotype instability.

As exact mechanisms allowing for consistent and reproducible oocyte activation and blastocyst formation are presently unclear, obstacles presently limiting generation of pSC lines would certainly be helped by a better understanding of these processes.

For example, recombination events occurring during meiotic stages in parthenogenesis can give rise to variable amounts of zygosity. Therefore, real-time visualization of these events would not only improve success rates for blastocyst formation and pn-hPSC cell line generation, but aid manipulation strategies aimed at achieving specific genetic and immunological characteristics of resulting pn-hPSC cells. Similarly, current SCNT approaches for deriving NT-hPSCs use oocytes from in vitro fertilization clinics. High failure rates, also due to aneuploidy, karyotype instability and/or inefficient nuclear reprogramming, requires greater numbers of oocytes for derivation of NT-hPSCs, and are still limited to generating cells that are not patient-specific. Thus, there is a great need in the art for techniques allowing consistent, efficient generation of immunocompatible and patient-specific hPSC using SCNT and/or parthenogenesis techniques.

Described herein are techniques for establishing immunocompatible and/or patient-specific hPSCs. In one aspect, efficient SCNT and/or parthenogenesis is described using improved techniques. This includes improvements in micromanipulation to reduce cellular damage, poloscope microscopy for real-time visualization without use of harsh staining agents and/or UV light exposure. More importantly, key barriers related to efficient blastocyst generation have been eliminated by application of methylation-altering agents promoting genomic activation within a reconstructed oocyte, along with addition of mitotic structures (e.g., centrioles) from sperm derivatives to promote blastocyst expansion. Application of these improved techniques allows realization of banks of pn-hPSCs expressing common human leukocyte antigen (HLA) haplotypes to provide cells immunologically compatible with wide segments of the population. In all aspects, pn-hPSCs and NT-hPSCs can be grown on animal protein-free culture media, as is vital for clinical applications eventually involving human patients, and provides transplantable cells that are genetically and epigenetically stable, and pluripotent.

SUMMARY OF THE INVENTION

Described herein is a method for generating a parthenote-derived human pluripotent stem cell line (pn-hPSC) including activating an oocyte by incubation in an activation medium, generating a parthenote by incubating the activated oocyte in a post-activation medium, forming a blastocyst by incubating the parthenote in a culture medium, and isolating inner cell mass (ICM) cells from the blastocyst, wherein the ICM cells are capable of further culturing as a pn-hPSC cell line. In other embodiments, the activation medium includes a calcium ionophore. In other embodiments, the calcium ionophore includes ionomycin, A23187, beauvericin, X-537A, and/or avenaciolide. In other embodiments, the post-activation medium includes 6-DMAP, puromycin, ethanol, cycloheximide (CHX), trichostatin A (TSA), and/or cytochalasin B (CB). In other embodiments, the post-activation medium includes a compound that does not prevent second polar body extrusion. In other embodiments, the oocyte includes a metaphase II (MII) stage oocyte. In other embodiments, the oocyte includes a metaphase I (MI) stage oocyte. In other embodiments, the oocyte includes a single pronuclear oocyte. In other embodiments, the pn-hPSC cell line is heterozygous. In other embodiments, the pn-hPSC cell line is homozygous. In other embodiments, the pn-hPSC cell line includes with a human leukocyte antigen (HLA) haplotype immunocompatible with at least 1% of a population. In other embodiments, the HLA haplotype includes HLA-A, HLA-B, and HLA-DR. In other embodiments, the method includes injecting sperm factors into the oocyte. In other embodiments, the oocyte is incubated in the presence of CARM 1 and/or Esrrb.

Further described herein is a parthenote-derived human pluripotent stem cell line (pn-hPSC) including pluripotent cells isolated from the inner cell mass (ICM) cells of a parthenote-derived blastocyst. In other embodiments, the parthenote-derived blastocyst includes a parthenote generated by incubating an oocyte in an activation medium. In other embodiments, the activation medium includes a calcium ionophore. In other embodiments, the calcium ionophore includes ionomycin, A23187, beauvericin, X-537A, and/or avenaciolide. In other embodiments, the parthenote-derived blastocyst includes a parthenote generated by incubating an activated oocyte in a post-activation medium. In other embodiments, the post-activation medium includes 6-DMAP, puromycin, ethanol, cycloheximide (CHX), trichostatin A (TSA), and/or cytochalasin B (CB). In other embodiments, the pn-hPSC cell line is heterozygous. In other embodiments, the pn-hPSC cell line is homozygous. In other embodiments, the pn-hPSC cell line includes pluripotent cells with a human leukocyte antigen (HLA) haplotype immunocompatible with at least 1% of a population. In other embodiments, the pluripotent cells express one or more markers from the group including stage-specific embryonic antigen-4 (SSEA-4), SSEA-3, tumor rejection antigen 1-81 (Tra-1-81), Tra-1-60, octamer binding transcription factor-4 (Oct-4), sex determining region Y-box-2 (Sox-2), nanog, zinc finger protein-42 (Rex-1/Zfp-42), lefty A, teratocarcinoma-derived growth factor (Tdgf), and telomeric repeating binding factor (Terf-1). In other embodiments, the pluripotent cells are capable of differentiating into cells derived from endodermal, mesodermal, and ectodermal germ layers. In other embodiments, the method further includes injecting sperm factors into the oocyte. In other embodiments, the oocyte is incubated in the presence of CARM 1 and/or Esrrb. Also described herein is a library of parthenote-derived human pluripotent stem cell lines (pn-hPSC) including one or more of the pn-hPSC cell lines.

Also described herein is a method of generating a nuclear transfer human pluripotent stem cell line (NT-hPSC), including removing the nucleus of an oocyte generating a nuclear transferred (NT) oocyte by adding at least one nucleus of at least one donor cell, activating the NT oocyte by incubation in an activation medium, generating a blastocyst from the activated NT oocyte, and isolating inner cell mass (ICM) cells from the blastocyst, wherein the ICM cells are capable of further culturing as a NT-hPSC cell line. In other embodiments, the method includes adding the at least one nucleus of at least one donor cell includes direct injection. In other embodiments, the method includes adding the at least one nucleus of at least one donor cell includes somatic cell fusion. In other embodiments, somatic cell fusion includes contact of Sendai virus, protein or extract thereof, with the at least one donor cell. In other embodiments, the at least one donor cell includes a somatic cell or germ cell. In other embodiments, the method is performed in the absence of ultraviolet light. In other embodiments, the method includes injecting sperm factors into the oocyte. In other embodiments, the oocyte is incubated in the presence of CARM 1 and/or Esrrb. Also described herein is an NT-hPSC cell line produced by the method, including removing the nucleus of an oocyte generating a nuclear transferred (NT) oocyte by adding at least one nucleus of at least one donor cell, activating the NT oocyte by incubation in an activation medium, generating a blastocyst from the activated NT oocyte, and isolating inner cell mass (ICM) cells from the blastocyst, wherein the ICM cells are capable of further culturing as a NT-hPSC cell line.

Also described herein is a method of nuclear transfer including generating a nuclear transferred (NT) oocyte by adding at least one nucleus of at least one donor cell to an oocyte, and removing the host nucleus of the oocyte. In other embodiments, the method includes activating the NT oocyte by incubation in an activation medium, generating a blastocyst from the activated NT oocyte, and isolating inner cell mass (ICM) cells from the blastocyst, wherein the ICM cells are capable of further culturing as a NT-hPSC cell line. In other embodiments, the method includes injecting sperm factors into the oocyte. In other embodiments, the oocyte is incubated in the presence of CARM 1 and/or Esrrb.

BRIEF DESCRIPTION OF THE FIGURES

Exemplary embodiments are illustrated in referenced figures. It is intended that the embodiments and figures disclosed herein are to be considered illustrative rather than restrictive.

DETAILED DESCRIPTION OF THE INVENTION

Figure 1:
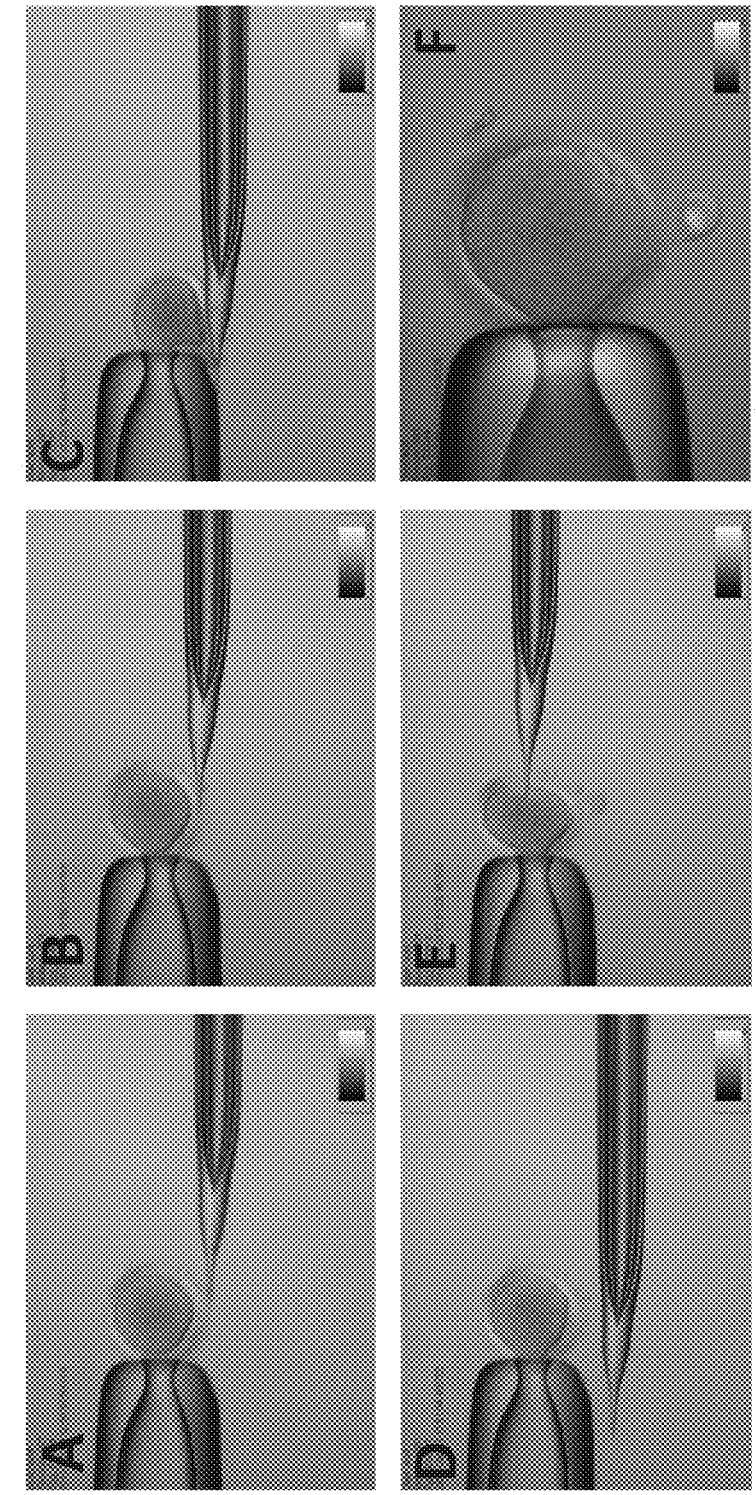
FIG. 1. Enculeation of oocytes. The contours of the "knife pipette" allow effective penetration of the zona pellucida via the (A) solid pointed fine tip, when the tip is advanced against (B) a lateral edge of a cell held stationary by holding pipette. (C) Penetration is followed by oocyte manipulation via the rounded pulled bead end for "pinching" of the fissure and (D) positioning of the polar body near the edge of the fissure. With the larger hollow tube body providing a bulk structure for the user to more easily grasp the knife pipette, (E) the polar body positioned near the fissure can then be (F) squeezed out for extraction.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods described herein. For purposes of the present invention, the following terms are defined below.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Modulation" or "modulates" or "modulating" as used herein refers to upregulation (i.e., activation or stimulation), down regulation (i.e., inhibition or suppression) of a response or the two in combination or apart.

"Pharmaceutically acceptable carriers" as used herein refer to conventional pharmaceutically acceptable carriers useful in this invention.

"Promote" and/or "promoting" as used herein refer to an augmentation in a particular behavior of a cell or organism.

"Subject" as used herein includes all animals, including mammals and other animals, including, but not limited to, companion animals, farm animals and zoo animals. The term "animal" can include any living multi-cellular vertebrate organisms, a category that includes, for example, a mammal, a bird, a simian, a dog, a cat, a horse, a cow, a rodent, and the like. Likewise, the term "mammal" includes both human and non-human mammals.

"Therapeutically effective amount" as used herein refers to the quantity of a specified composition, or active agent in the composition, sufficient to achieve a desired effect in a subject being treated. A therapeutically effective amount may vary depending upon a variety of factors, including but not limited to the physiological condition of the subject (including age, sex, disease type and stage, general physical condition, responsiveness to a given dosage, desired clinical effect) and the route of administration. One skilled in the clinical and pharmacological arts will be able to determine a therapeutically effective amount through routine experimentation.

"Treat," "treating" and "treatment" as used herein refer to both therapeutic treatment and prophylactic or preventative measures, wherein the object is to prevent or slow down (lessen) the targeted condition, disease or disorder (collectively "ailment") even if the treatment is ultimately unsuccessful. Those in need of treatment may include those already with the ailment as well as those prone to have the ailment or those in whom the ailment is to be prevented.

As described, isolation and characterization of human pluripotent stem cells (hPSCs) and breakthroughs in parthenogenesis and/or somatic cell nuclear transfer (SCNT) technology in mammals have raised the possibility of generating potentially unlimited sources of hPSCs for use in research, with potential applications in tissue repair and transplantation medicine.

With respect to parthenogenesis, elimination of paternal contribution in resulting cells can be applied, in some instances, to minimize major histocompatibility complex (MHC) diversity. This allows for generation of parthenote-derived human pluripotent stem cells (pn-hPSC) that are broadly immunocompatible with wide swaths of patient populations. Generating homozygous pn-hPSC cell lines further improves potential immunocompability by eliminating hetereozygotic variation. In the instance of homozygotic expression of only one set of alleles, this allows the resulting pn-hPSC lines to be more readily matched to patients. For example, it has been reported that a panel of as few as ten HLA homozygous pn-hPSC lines selected for common haplotypes could provide a complete HLA-A. HLA-B, and HLA-DR match for nearly 40% of UK recipients and a beneficial match for nearly 65%. Similar benefits exist when considering application of SCNT in a therapeutic setting. Cells obtained via SCNT (NT-hPSCs) would carry the nuclear genetic material of the patient and in this regard, are individual patient-specific. This form of autologous transplantion allows transplation of cells into a patient with significantly reduced risk of immune rejection.

Parthenogenesis and SCNT techniques both involve artificial oocyte activation, which relies on mimicking the calcium signaling changes that occur during natural sperm fertilization. Normal oocyte development relies on high levels of metaphase promoting factor (MPF) activity to arrest oocytes at the metaphase II (MII) stage. Arrest of the MII oocyte is disrupted by changes in intracellular calcium ion (Ca2+) levels due to sperm entry. This is followed by targeted degradation of cyclin B (a MPF regulatory subunit), which releases the oocyte from arrest, pronuclei formation, and the initiation of meiotic and mitotic processes.

As a first step, parthenogenic oocyte activation relies on artificial calcium-alteration strategies to release a cultured oocyte from arrest. Examples include addition of calcium ionophores, lipid-soluble molecules that transport ions across the lipid bilayer, such as ionomycin and A23817. Alternative strategies rely on electrical activation, or direct injection of ions. A second key step in parthenogenesis involves maintaining MPF/cyclin B inhibition, which prevents extrusion of the second polar body extrusion (2PBE).

This leads to generation of a diploid (2 maternal genome) parthenote, which can be further cultivated into a blastocyst for pn-hPSC cell isolation. As related to SCNT, reconstruction of a nuclear transferred (i.e., reconstructed) oocyte is also followed by oocyte activation using calcium alteration techniques.

However, there are significant limitations in each of these current SCNT and/or parthenogenesis techniques. For example, while it has been reported that addition of protein phosphatase inhibitor caffeine to sheep oocytes increases the activity of maturation-promoting factor (MPF) and mitogen-activated protein kinases (MAPKs) and similar benefits have been reported in monkey oocytes, the frequency of blastocyst formation is not enhanced. Further, calcium activation via calcium ionophore, electrical activation, or direct injection does not produce the same timing, spatial regulation, or duration of calcium oscillations as natural fertilization. Adding further complexity is that the effect on calcium also appears to be species specific. In some instances, the use of additional treatment with kinase inhibitors like 6-diemthylaminopurine (6-DMAP), ethanol, and protein synthesis inhibitors like cycloheximide (CHX) are used to enhance MPF inactivation, as informed by bovine, mouse, and other animal models. While effective, addition of such agents may present other drawbacks. For example, whereas 6-DMAP addition during parthenogenic activation prevents extrusion of the second polar body and generation of diploid cells, this approach does not allow for the generation of the more widely immunocompatible homozygous hPSC cell lines. Further, As related to SCNT, existing techniques are hampered by aneuploidy and inefficient nuclear reprogramming, leading to high rates of developmental arrest and cell death. Structural and genotoxic stress during enucleation, reconstruction, along with oocyte activation inefficiencies, and defects during the first mitotic division of the SCNT zygote have all been proposed to contribute to poor development rates using SCNT.

To establish effective techniques for generating immunocompatible and/or patient specific hPSCs, the inventors compared different protocols, with variations in: 1) reconstruction, 2) activation, and 3) donor cell. An improved understanding of all three aspects would provide effective SCNT techniques, whereas improved methods for oocyte activation would provide superior approaches for parthenogensis. Therefore, the techniques described herein provide comparison of performance of variations in reconstruction, activation, and donor cell choice, and successfully identify effective conditions for human parthenogenesis and/or SCNT.

Described herein is a method for somatic nuclear transfer (SCNT). In one embodiment, the method for SCNT includes enucleation of an oocyte, transfer of one or more donor nuclei, activation of the reconstructed nuclear transferred oocyte (embryo), and optionally, further culturing into blastocyst, and derivation of pluripotent stem cells (pSCs) from the blastocyst. In other embodiments, this includes isolating one or more donor nucleus for injection into the enucleated oocyte.

In various embodiments, enucleating an oocyte includes removal of a metaphase II (MII) stage egg spindle. In various embodiments, the first polar body (1PBE) is removed. In another embodiment, the method includes denuding the cumulus cells before the completion of maturation. In one embodiment, the oocyte is monitored with real-time, non-UV light based monitoring for 1PBE. In another embodiment, the monitoring occurs in the absence of a staining or labeling agent, such as Hoechst staining. In one embodiment, this includes use of a poloscope, such as a Research Instruments (CRi) Oosight™ imaging system. For example, this can include visualizing the zona pellucida and the spindle complex in the harvested MII oocyte harvested with 545 nm polarized light. In another embodiment, enucleating an oocyte includes use of a contoured micropipette allows for both puncture of an oocyte membrane and removal of a 1PBE from the oocyte. In another embodiment, enucleating an oocyte includes use of a piezoelectric drill. In other embodiments, enucleation is performed in a enucleation medium containing cytochalasin B and optionally, a protein phosphatase inhibitor such as caffeine.

In another embodiment, transfer of a donor nucleus includes use of an agent that alters oocyte cell membrane structure. In one embodiment, enucleating an oocyte trough use of an agent that alters oocyte cell membrane structure includes fusion with a somatic cell. For example, transfer of a donor nucleus may include providing 3-4 donor cells an injection pipette (e.g., 12 um diameter), expelling donor cells in a quantity of solution containing a paramyxovirus or paramyxovirus protein, such as Sendai virus envelope protein. This is followed by retrieving the cells using the injection pipette with a distance (4-5 cell length) separating the donor cells arranged linearly, holding an oocyte with a holding pipette, advancing the injection pipette with donor cells into the oocyte. In various embodiments, advancing the injection pipette includes no disruption of the oolema plasma membrane, and insertion of one nuclear donor cell in the perivitelline space, the space between the zona pellucida and the cell membrane, of an oocyte to contact the nuclear donor cells with the oolema plasma membrane, which sits beneath the zona pellucida. In various embodiments, withdrawal of the pipette does not disturb contact between oolema and donor cell. In various embodiments, the oocytes are further incubated. In various embodiments, the cells are fused 1, 2, 3, 4, 5, 6, 7, 8, 9, 10, 11, 12, 13, 14, 15 or more minutes after the donor cell insertion. In various embodiments, the cells are fused 10 min after the donor cell insertion. Optionally, the above procedures are repeated for cells not successfully fused. In various embodiments, a poloscope, such as Oosight™ imaging system, is used throughout the process.

In one embodiment, transfer of a donor nucleus may include electrical cell manipulation, such as electrofusion. In other embodiments, the method may include isolating the nucleus of a somatic nuclear donor, stem cell nuclear donor, and germ cell nuclear donor. In other embodiments, the method may include isolating a somatic nucleus for SCNT, followed by injection of one or more donor nuclei via pipette or piezoelectric injection. In various embodiments, the donor nuclei is from cells such as skin fibroblasts, white blood cells, hair follicles, or any other somatic cell nuclear donor. In another embodiment, the present invention describes a method including isolation and preparation of a nucleus from a germ cell donor. In different embodiments, isolation of a nucleus includes a tissue biopsy, blood draw, or other means of obtaining a tissue sample, processing this tissue with mechanical disassociation, collagenase digestion, washing, centrifuge-based density gradient separation, and/or culturing with standard culture medium.

In other embodiments, the method may include isolating and/or modifying the nucleus of a somatic nuclear donor, stem cell nuclear donor, and germ cell nuclear donor. In various embodiments, this includes methylation-altering agents, such as epigenetic chromatin and β histone modification agents, and/or DNA modification agents. In certain embodiments, this includes protein arginine methyl-transferase (PRMT1) and coactivator-associated arginine methyltransferase 1 (CARM1/PRMT4) or orphan nuclear receptor estrogen related receptor β (Esrrb) protein. In certain embodiments, the methylation-altering agents and/or DNA modification are expressed as modified recombinant proteins. For example, CARM1 and Esrrb can be modified with 7× arginine (7R)-cell-penetrating peptides (CPPs), or any other proteins known to one of ordinary skill enhance penetration of proteins and peptides across cellular and nuclear membranes, enhance binding and/or transactivation to DNA. In other embodiments, the method includes epigenetically reprogramming the nuclear donor cells using transcription factor-based reprogramming with octamer binding transcription factor-4 (Oct-4), sex determining region Y-box-2 (Sox-2), nanog, Kruppel-like factor-4 (Klk-4), MyoD, c-Myc, zinc finder protein-42 (Rex-1/Zfp-42), lefty A, teratocarcinoma-derived growth factor (Tdgf), and/or telomeric repeating binding factor (Terf-1). In various embodiments, the method includes direct piezoelectric injection, viral injection, liposomal injection, or other methods of intracytoplasmic injection. In various embodiments, the transcription factors may be delivered in the form of mRNA, protein, and/or cellular extracts that can be applied prior to the nuclear transfer to the enucleated oocyte. In other embodiments, the method includes the use of HDAC inhibitors (Class I, II, and III), or DNMT3a and DNMT3b inhibitors.

In another embodiment, the present invention describes a method of activating a reconstructed nuclear transferred oocyte. In one embodiment, activation of a reconstructed nuclear transferred oocyte incudes treating nuclear transfer oocytes in activation medium for 5 min at 37° C., following by washing in cleavage medium. In different embodiments, the activation medium is a HEPES-free medium, protein-free medium, G1 or G2 medium, cleavage medium, cleavage assist medium, IVF medium, blastocyst formation medium, or global human embryo culture medium. In certain embodiments, the activation medium includes a calcium ionophore. In different embodiments, the calcium ionophore is ionomycin, A23187, beauvericin, X-537A, avenaciolide, monomacrocyclic polyethers, or macrobiocyclic compounds or cryptates. In different embodiments, the activation medium includes an alcohol, such as ethanol. In different embodiments, the activation medium includes thimerosal. In various embodiments, the activation medium includes 1, 2, 3, 4, 5, 5 or more µM ionomycin. In other embodiments, the method includes electrical activation of an MII stage oocyte. In one embodiment, electrical activation includes electrical pulse in electrofusion medium. In various embodiments, the electrofusion medium includes 0.1-0.5 M mannitol, 0.01-1 mM MgSO4.7H2O, 0.01-1 mg/ml polyvinyl alcohol, 1-10 mg/ml human serum albumin, 0.005-0.5 mM CaCl2.2H2O). In one embodiment, the electrofusion medium includes 0.3 M mannitol, 0.1 mM MgSO4.7H2O, 0.1 mg/ml polyvinyl alcohol, 3 mg/ml human serum albumin, 0.05 mM CaCl2.2H2O). In one embodiment, activating the reconstructed nuclear transferred oocyte allows chromatin condensation, spindle formation, and chemical activation. In other embodiments, combinations of electrical pulses, optionally followed by 6-DMAP may be applied, for example (2×50 µs DC pulses, 2.7 kV/CM) in 0.25M d-sorbitol buffer and 6-DMAP (2 mM, 4 hours). In other embodiments the various described media, such as HEPES-free medium, protein-free medium, G1 or G2 medium, cleavage medium, cleavage assist medium. IVF medium, blastocyst formation medium, or global human embryo culture medium optionally includes a growth factor such as GM-CSF or IGF1. In various embodiments, the growth factor can be added 1, 2, 3, 4, 5, 6, 7 or more days after nuclear transfer.

In various embodiments, the nuclear transfer oocytes are treated in post-activation medium to complete activation. In different embodiments, activated reconstructed nuclear transferred oocytes are then incubated in post-activation medium. In different embodiments, the post-activation medium is a HEPES-free medium, protein-free medium, G1 or G2 medium, cleavage medium, cleavage assist medium, IVF medium, blastocyst formation medium, or global human embryo culture medium. In different embodiments, the post-activation medium includes 6-DMAP, puromycin, ethanol, cycloheximide (CHX), trichostatin A (TSA), and/or cytochalasin B (CB). In different embodiments, the activated oocytes are incubation in the post-activation medium for less than 30, 30-45, 45-60, 60-90, 90-120, 120-150, 150-180, 180-210, 210-240, 240-270, 300-330, 330-360, 360-390, or more than 390 minutes. In certain embodiments, the activated oocytes are incubated for 240, 300, or 360 minutes. In various embodiments, activation and post-activation steps are performed under reduced oxygen conditions. In certain embodiments, reduced oxygen conditions include about 80-85%, 85-90%. 90-95%, 95% or more N2, about 1%, 2%, 3%, 4%, 5%, 6%, 7%, 8%, 9%, 10% or more O2, and about 1%, 2%, 3%, 4%, 5%, 6%, 7%, 8%, 9%, or 10% or more CO2. In certain embodiments, reduced oxygen conditions include about 90% N2, about 5% O2, and about 5% CO2. In various embodiments, the post-activation medium includes 1, 2, 3, 4, 5, 5 or more mM 6-DMAP in cleavage medium for 1, 2, 3, 4, 5, 5 or more hours, incubated in a temperature such as 37° C. in a gas mixture, such about 90% N2, about 5% O2, and about 5% CO2.

After incubation in post-activation medium, the post-activated oocytes are incubated in a wash medium. In different embodiments, the wash medium is a HEPES-free medium, protein-free medium, G1 or G2 medium, cleavage medium, cleavage assist medium, IVF medium, blastocyst formation medium. In another embodiment, the culture medium does not require serial medium change, such as global human embryo culture medium. In certain embodiments, the wash medium includes TSA. In certain embodiments, the post-activated oocytes are incubated in the wash medium including TSA for 240, 300, or 360 minutes. In one embodiment, the post-activated reconstructed nuclear transferred oocyte is washed, and further cultured. In one embodiment, the post-activated reconstructed nuclear transferred oocyte washed in a 6-DMAP free medium. In other embodiments the various described media, such as HEPES-free medium, protein-free medium, G1 or G2 medium, cleavage medium, cleavage assist medium, IVF medium, blastocyst formation medium, or global human embryo culture medium optionally includes a growth factor such as GM-CSF or IGF1. In various embodiments, the growth factor can be added 1, 2, 3, 4, 5, 6, 7 or more days after nuclear transfer.

In another embodiment, activation and/or post-activation steps includes addition of factors isolated from sperm, derivatives and extracts thereof. In one embodiment, human sperm factors are injected into the activated reconstructed eggs using any of the described injection methods. In one embodiment, human sperm factors are injected into the post-activated reconstructed eggs using any of the described injection methods. In various embodiments, after about one, two, three, or four days, the post-activated reconstructed nuclear transferred oocyte is switched to cleavage medium. In a certain embodiment, after about one day post-activated the reconstructed nuclear transferred oocyte is switched to cleavage medium. In various embodiments, sperm factors include for example, factors from isolating cell proteins present inside or outside of sperm cells. In one embodiment, whole sperm extracts are obtained using detergents and mechanical blending of ejaculated sperm. In another embodiment, whole sperm cell extracts are treated with DNAase I and RNAase. In another embodiment, the crude extract is washed in buffer and centrifugation (20,000 g for 2 hours). In other embodiments, fresh ejaculated human sperm is collected and centrifuge at 900 g for 10 min to remove seminal plasma, followed by resuspesion of pellet in Sperm-TALP containing 5 mg/mL bovine serum albumin, and centrifuged at the same setting, followed by removal of supernatant and resuspension of the pellet to a final concentration of $20 \times 10^8$ sperm/mL in nuclear isolation medium ((NIM: 125 mM KCl, 2.6 mM NaCl, 7.8 mM Na2HPO4, 1.4 mM KH2PO4, 3.0 mM EDTA disodium salt; pH 7.45 and centrifuged to remove Sperm-TALP. After Sperm-TALP is removed, resuspension of the pellet to the same volume with NIM containing 1 mM dithiothreitol, 100 mM leupeptin, 100 mM antipain, and 100 mg=mL soybean trypsin inhibitor is followed by four cycles of freezing (5 min per cycle in liquid N2) and thawing (5 min per cycle at 15° C.), with compact sperm pellet formation at 20,000× for 50 min at 2° C. Finally, the resulting supernatant is carefully removed, aliquoted, and kept at −80° C. until use.

In various embodiments, the post-activated reconstructed nuclear transferred oocyte is further cultured into a blastocyst. In one embodiment, the post-activated reconstructed nuclear transferred oocyte is further cultured in SAGE cleavage medium, such as Quinn's medium. In another embodiment, the medium promotes pluripotency, such as 3i medium (Neuro basal medium 50%, DMEM/F-12 50%, N2 supplement 1/200 v/v, B27 supplement 1/100 v/v, 100 mM L-glutamine 1/100 v/v, 0.1M ß-ME 1/1000 v/v, SU5402 (FGFR inhibitor) 2 µM, PD184352 (ERK cascade inhibitor) 0.8 µM, CHIR99021 (GSK3 inhibitor) 3 µM) or modified 3i medium (including PD0325901 (MAPK inhibitor) 0.4 µM). In one embodiment, the further culturing is for 1, 2, 3, 4, 5, 5 or more days. In one embodiment, additional culturing is provided in a culture medium with reprogramming factors and/or methylation-altering agents. In various embodiments, the additional culturing is in G2 medium supplemented with CARM1 and/or Esrrb) for 3 days. For example, CARM1 and/or Esrrb can each be provided at a concentration in the medium of 0.5, 1, 1.5, 2, 2.5, 3, 3.5, 4, 4.5, 5 or more µg/ml. In some embodiments, CARM1 and/or Esrrb are each provided at a concentration in the medium at 2 µg/ml.

In various embodiments, further culturing into a blastocyst and derivation of pluripotent stem cells (pSCs) from the blastocyst includes treat a cultured blastocyst with acidic Tyrode's solution to remove zona pellucida (ZP). In various embodiments, treatment is for a few (e.g., 1-5) seconds. In various embodiments, removal of the ZP is followed by wash in Hepes-HTF medium. In various embodiments, isolation of the inner cell mass (ICM) includes discarding trophoblast of the blastocyst. In various embodiments, the ICM cells are plated mouse embryonic feeders (MEFs) which are prepared one day before the plating. In some embodiments, whole blastocysts are plated on MEFs. For example, this method includes denuding the zona pellucida of the blastocyst. In various embodiments, the method includes removal of the zona pellucida of blastocysts with 0.05, 0.1, 0.2, 0.3, 0.4, 0.5, 0.6, 0.7, 0.8, 0.9, or 1% pronase in Hepes-HTF medium. In one embodiment, the method includes removal of the zonae pellucida of blastocysts with 0.5% pronase in Hepes-HTF medium. In another embodiment, the method includes application of pronase in TH3 (SAGE Blastocyst medium), medium for 1-10, 10-20, 20-30, 30-60, 60-120, 120-180, or >180 seconds. In another embodiment, the method includes application of 0.5% pronase in HTF medium for 30-60 seconds. In one embodiment, the blastocyst is derived from a parthenote obtained from parthenogenesis of an oocyte. In one embodiment, the hPSC line is a parthenote-derived human pluripotent hPSC (pn-hPSC) cell line. In another embodiment, the blastocyst is derived from a reconstructed nuclear transferred oocyte obtained from somatic cell nuclear transfer (SCNT) of a donor cell nucleus into a recipient oocyte. In one embodiment, the hPSC line is a somatic cell nuclear transfer human pluripotent hPSC (NT-hPSC) cell line. In another embodiment, the present invention describes a method of immunosurgery, including mechanical dispersion of the inner cell mass (ICM) from trophectodermal cells. In various embodiments, a denuded blastocyst is treated with rabbit anti-human spleen serum for about 10, 20, 25, 30, 35, 40, 45, or 60 minutes at 37° C. In one embodiment, a denuded blastocyst is treated with rabbit anti-human spleen serum for about 30 minutes at 37° C. In one embodiment, the method includes washing the denuded blastocyst with TH3 (SAGE Blastocyst medium), incubation in guinea pig complement reconstructed with HECM-9 (SAGE Blastocyst medium), for 30 min at 37° C. In different embodiments, zonae pellucidae of expanded blastocysts are be removed by brief exposure (45-60 seconds) to 0.5% pronase or acidic Tyrode's solution in TH3 (hepes-HTF) medium. In one embodiment, the method optionally includes mechanical cell dispersion using small bore pipetting or laser assisted hatching method using Zilos-tk Unit (Hamilton Thorne) to separate inner cell mass cells from the trophoectodermal cells.

In one embodiment, the method for SCNT includes enucleation of oocytes, transfer of donor nucleus, activation of a reconstructed nuclear transferred oocyte, and optionally, further culturing into a blastocyst, derivation of pluripotent stem cells (pSCs) from the blastocyst. In one embodiment, enucleating an oocyte includes removal of a metaphase II stage egg spindle. In various embodiments, the first polar body (1PBE) is removed. In one embodiment, transfer of a donor nucleus includes providing 3-4 donor cells an injection pipette (e.g., 12 um diameter), expelling donor cells in a quantity of solution containing Sendai virus envelope protein, retrieving the cells using the injection pipette with a distance (4-5 cell length) separating the donor cells arrange linearly, hold an oocyte with a holding pipette, advancing the injection pipette with donor cells into the oocyte. In various embodiments, advancing the injection pipette includes no disruption of the oolema, and insertion of one nuclear donor cell in the perivitelline space to contact the nuclear donor cells with the oolema. In various embodiments, withdrawal of the pipette does not disturb contact between oolema and donor cell. In various embodiments, the oocytes is further incubated. In various embodiments, the cells are fused 10 min after the donor cell insertion. Optionally, the above procedures are repeated for cells not successfully fused. In various embodiments, a poloscope, such as Oosight™ imaging system, is used throughout the process. In other embodiments, enucleation is performed in a enucleation medium containing cytochalasin B and optionally, a protein phosphatase inhibitor such as caffeine. In other embodiments, the method includes use of a proteasome inhibitor, such as MG132. In certain embodiments, the method of SCNT can include, transfer of one more donor nuclei thereafter followed by enucleation of the oocyte.

In one embodiment, activation of a reconstructed nuclear transferred oocyte includes treating a reconstructed nuclear transferred oocyte in activation medium for 5 min at 37° C., following by washing in cleavage medium. In various embodiments, the activation medium includes 5 µM ionomycin. In various embodiments, the nuclear transfer oocytes are treated in post-activation medium to complete activation. In various embodiments, the post-activation medium includes 2 mM 6-DMAP in cleavage medium for 4 hrs at 37° C. in 5% CO2/5% N2/90% N2 atmosphere. In one embodiment, the activated nuclear transfer oocyte is washed, and further cultured. In one embodiment, the post-activated reconstructed nuclear transferred oocyte is washed in a 6-DMAP free medium. In one embodiment, the post-activated reconstructed nuclear transferred oocyte is further cultured in SAGE cleavage medium. In one embodiment, the further culturing is for 2 days. In one embodiment, additional culturing is provided in a culture medium with reprogramming factors and/or methylation-altering agents. In various embodiments, the additional culturing is in G2 medium supplemented with CARM1 and/or Esrrb) for 3 days. In various embodiments, the activated nuclear transfer oocyte is further cultured into a blastocyst. In various embodiments, further culturing into a blastocyst, and derivation of pluripotent stem cells (pSCs) from the blastocyst includes treat a cultured blastocyst with acidic Tyrode's solution (e.g., pH 2.0) to remove zona pellucida (ZP). In various embodiments, treatment is for a few (e.g., 1-5) seconds. In various embodiments, removal of the ZP is followed by wash in Hepes-HTF medium. In various embodiments, isolation of the inner cell mass (ICM) includes discarding trophoblast of the blastocyst. In various embodiments, the ICM cells are plated mouse embryonic feeders (MEFs) which are prepared one day before the plating. In some embodiments, whole embryos are plated on MEFs. In various embodiments, PSC derivation medium is composed of knockout-DMEM supplemented with serum replacement (5% SR, Invitrogen), FBS (10%, Hyclone), plasmamate (5%), bFGF (32 ng/ml), and human LIF (2000 units/ml, Sigma-Aldrich).

Also described herein is a human pluripotent stem cell line derived from somatic cell nuclear transfer (NT-hPSC). In various embodiments, the NT-hPSC is genetically identical, or nearly identical, to a donor nucleus. In different embodiments, the NT-hPSC cell line contains a normal 46 chromosome, XX/XY karyotype. In different embodiments, the NT-hPSC cell line is capable of forming all three embryonic germ layers. In different embodiments, the NT-hPSC cell line expresses one or more pluripotent markers, pluripotent markers including stage-specific embryonic antigen-4 (SSEA-4), SSEA-3, tumor rejection antigen 1-81 (Tra-1-81), Tra-1-60, octamer binding transcription factor-4 (Oct-4), sex determining region Y-box-2 (Sox-2), nanog, zinc finder protein-42 (Rex-1/Zfp-42), lefty A, teratocarcinoma-derived growth factor (Tdgf), telomeric repeating binding factor (Terf-1), and developmental pluripotency-associated gene 2 (Dppa-2). In different embodiments, the NT-hPSC cell line does not contain a recessive lethality. In different embodiments, the NT-hPSC cell line possesses high alkaline phosphatase (AP) and/or telomerase activity. In different embodiments, the NT-hPSC cell line is capable of forming embryoid bodies in suspension and/or teratomas including cells derived from all three embryonic germ layers in an immunodeficient animal.

Also described herein is a method for parthenogenesis of a human oocyte. In one embodiment, the method includes incubating a metaphase II (MII) stage oocyte in an activation medium to initiate formation of a parthenogenic oocyte. In certain embodiments, the activation medium includes a calcium ionophore. In different embodiments, the calcium ionophore is ionomycin, A23187, beauvericin, X-537A, avenaciolide, monomacrocyclic polyethers, or macrobiocyclic compounds or cryptates. In different embodiments, the activation medium includes an alcohol, such as ethanol. In different embodiments, the activation medium includes thimerosal. In different embodiments, the activation medium is a activation medium is a HEPES-free medium, protein-free medium, G1 or G2 medium, cleavage medium, cleavage assist medium, IVF medium, blastocyst formation medium, or global human embryo culture medium. In other embodiments, the method includes electrical activation of an MII stage oocyte. In one embodiment, electrical activation includes electrical pulse in electrofusion medium. In various embodiments, the electrofusion medium includes 0.1-0.5 M mannitol, 0.01-1 mM MgSO4.7H2O, 0.01-1 mg/ml polyvinyl alcohol, 1-10 mg/ml human serum albumin, 0.005-0.5 mM CaCl2.2H2O). In one embodiment, the electrofusion medium includes 0.3 M mannitol, 0.1 mM MgSO4-7H2O, 0.1 mg/ml polyvinyl alcohol, 3 mg/ml human serum albumin, 0.05 mM CaCl2.2H2O). In other embodiments, one or more oocytes are first injected with sperm factors, and then electrically activated.

In certain embodiments, the MII stage oocyte is incubated in the activation medium for 1, 2, 3, 4, 5, 6, 7, 8, 9, 10, or more than 10 minutes at 30° C., 31° C., 32° C., 33° C., 34° C., 35° C., 36° C., 37° C., 38° C., 39° C., 40° C., or more than 40° C. temperature followed by washing in a wash medium. In certain embodiments, the MII stage oocyte is exposed to the calcium ionophore for 5 minutes at 37° C. temperature, followed by washing in a wash medium. In different embodiments, the wash medium is a HEPES-free medium, protein-free medium, G1 or G2 medium, cleavage medium, cleavage assist medium, IVF medium, blastocyst formation medium.

In different embodiments, activated parthenogenic oocytes are then incubated in post-activation medium. In different embodiments, the post-activation medium is a HEPES-free medium, protein-free medium, G1 or G2 medium, cleavage medium, cleavage assist medium, IVF medium, blastocyst formation medium, or global human embryo culture medium. In different embodiments, the post-activation medium includes 6-DMAP, puromycin, ethanol, cycloheximide (CHX), trichostatin A (TSA), and/or cytochalasin B (CB). In different embodiments, the activated parthenogenic oocytes are incubation in the post-activation medium for less than 30, 30-45, 45-60, 60-90, 90-120, 120-150, 150-180, 180-210, 210-240, 240-270, 300-330, 330-360, 360-390, or more than 390 minutes. In certain embodiments, the activated parthenogenic oocytes are incubated for 240, 300, or 360 minutes. In various embodiments, activation and post-activation steps are performed under reduced oxygen conditions. In certain embodiments, reduced oxygen conditions include about 80-85%, 85-90%. 90-95%, 95% or more N2, about 1%, 2%, 3%, 4%, 5%, 6%, 7%, 8%, 9%, 10% or more O2, and about 1%, 2%, 3%, 4%, 5%, 6%, 7%, 8%, 9%, or 10% or more CO2. In certain embodiments, reduced oxygen conditions include about 90% N2, about 5% 02, and about 5% CO2.

After incubation in post-activation medium, the post-activated parthenogenic oocytes are incubated in a wash medium. In different embodiments, the wash medium is a HEPES-free medium, protein-free medium, G1 or G2 medium, cleavage medium, cleavage assist medium, IVF medium, blastocyst formation medium. In another embodiment, the culture medium does not require serial medium change, such as global human embryo culture medium. In certain embodiments, the wash medium includes TSA. In certain embodiments, the post-activated parthenogenic oocytes are incubated in the wash medium including TSA for 240, 300, or 360 minutes.

After incubation in wash medium, post-activated parthenogenic oocytes are transferred to culture medium. In different embodiments, the culture medium is a HEPES-free medium, protein-free medium, G1 or G2 medium, cleavage medium, cleavage assist medium, IVF medium, blastocyst formation medium. In another embodiment, the culture medium does not require serial medium change, such as global human embryo culture medium. In different embodiments, post-activated parthenogenic oocytes can be cultured in cleavage medium for 1, 2, 3, 4, 4 or more days. In certain embodiments, culturing in cleavage medium is for 2 days. After culturing in cleavage medium, oocytes are cultured in blastocyst formation medium for 1, 2, 3, 4, 4 or more days. In certain embodiments, culturing in blastocyst formation medium is for 3 days.

In one embodiment, activation of a oocyte includes incubating activation medium for 5 min at 37° C., following by washing in cleavage medium. In various embodiments, the activation medium includes 5 μM ionomycin. In various embodiments, the oocytes are treated in post-activation medium to complete activation. In various embodiments, the post-activation medium includes 2 mM 6-DMAP in cleavage medium for 4 hrs at 37° C. in 5% CO2/5% N2/90% N2 atmosphere. In one embodiment, the activated is washed, and further cultured. In one embodiment, the activated parthenogenic oocytes are washed in a 6-DMAP free medium. In one embodiment, the activated parthenogenic oocytes are further cultured in SAGE cleavage medium, such as Quinn's medium. In another embodiment, the medium promotes pluripotency, such as 3i medium (Neuro basal medium 50%, DMEM/F-12 50%, N2 supplement 1/200 v/v, B27 supplement 1/100 v/v, 100 mM L-glutamine 1/100 v/v, 0.1M ß-ME 1/1000 v/v, SU5402 (FGFR inhibitor) 2 μM, PD184352 (ERK cascade inhibitor) 0.8 μM, CHIR99021 (GSK3 inhibitor) 3 μM) or modified 3i medium (including PD0325901 (MAPK inhibitor) 0.4 μM). In one embodiment, the further culturing is for 2 days. In one embodiment, additional culturing is provided in a culture medium with reprogramming factors and/or methylation-altering agents. In various embodiments, the additional culturing is in G2 medium supplemented with CARM1 and/or Esrrb) for 3 days. In various embodiments, the activated parthenogenic oocyte is further cultured into a blastocyst. In various embodiments, further culturing into a blastocyst and derivation of pluripotent stem cells (pSCs) from the blastocyst includes treat a cultured blastocyst with acidic Tyrode's solution (e.g., pH 2.0) to remove zona pellucida (ZP). In various embodiments, treatment is for a few (e.g., 1-5) seconds. In various embodiments, removal of the ZP is followed by wash in Hepes-HTF medium. In various embodiments, isolation of the inner cell mass (ICM) includes discarding trophoblast of the blastocyst. In various embodiments, the ICM cells are plated mouse embryonic feeders (MEFs) which are prepared one day before the plating. In some embodiments, whole embryos are plated on MEFs. In various embodiments, PSC derivation medium is composed of knockout-DMEM supplemented with serum replacement (5% SR, Invitrogen), FBS (10%, Hyclone), plasmamate (5%), bFGF (32 ng/ml), and human LIF (2000 units/ml, Sigma-Aldrich).

Also described herein is a parthenote-derived human pluripotent stem cell (pn-hPSC) line. In different embodiments, the pn-hPSC cell line is derived from a heterozygous or homozygous oocyte. In certain embodiments, the heterozygous pn-hPSC cell line includes allelic variations of HLA haplotypes with HLA serotypes immunocompatible with 1%, 2%, 3%, 4%, 5%, 6% or more of an ethnic population, as determined by allelic variation frequency in an ethnic population. In certain embodiments, the homozygous pn-hPSC cell line was derived using parthenogenesis of a one-pronuclear oocyte. In certain embodiments, the homozygous pn-hPSC cell line was derived using parthenogenesis of a one-pronuclear homozygous oocyte. In other embodiments, the homozygous pn-hPSC cell line was derived using parthenogenesis including second polar body extrusion. In certain embodiments, the homozygous pn-hPSC cell line includes HLA haplotypes with HLA serotypes immunocompatible with 1%, 2%, 3%, 4%, 5%, 5% or more of an ethnic population, as determined by allelic variation frequency in an ethnic population. For example, the HLA haplotype A*01, B*08, DRB1*03 is present at a frequency of over 5% in Caucasian populations. In other embodiments, the HLA-serotypes include allelic variants of HLA-A, HLA-B, HLA-DP, HLA-DM, HLA-DOA, HLA-DOB, HLA-DQ, and HLA-DR In other embodiments, the HLA-serotypes include allelic variants of HLA-A, HLA-B, and HLA-DR In different embodiments, the pn-hPSC cell line is derived from a metaphase I (MI) stage oocyte. In different embodiments, the pn-hPSC cell line is derived from a metaphase II (MII) stage oocyte. In different embodiments, the pn-hPSC cell line contains a mitochondrial genome identical or nearly identical to the donor oocyte.

In different embodiments, the pn-hPSC cell line contains a normal 46 chromosome, XX karyotype. In different embodiments, the pn-hPSC cell line is capable of forming all three embryonic germ layers. In different embodiments, the pn-hPSC cell line expresses one or more pluripotent markers, pluripotent markers including stage-specific embryonic antigen-4 (SSEA-4), SSEA-3, tumor rejection antigen 1-81 (Tra-1-81), Tra-1-60, octamer binding transcription factor-4 (Oct-4), sex determining region Y-box-2 (Sox-2), nanog, zinc finger protein-42 (Rex-1/Zfp-42), lefty A, teratocarcinoma-derived growth factor (Tdgf), telomeric repeating binding factor (Terf-1), and developmental pluripotency-associated gene 2 (Dppa-2). In different embodiments, the pn-hPSC cell line does not contain a recessive lethality. In different embodiments, the pn-hPSC cell line possesses high alkaline phosphatase (AP) and/or telomerase activity. In different embodiments, the pn-hPSC cell line is capable of forming embryoid bodies in suspension and/or teratomas in an immunodeficient animal.

Also described herein is a library of parthenote-derived human pluripotent stem cell (pn-hPSC). In certain embodiments, the library includes 1, 2, 3, 4, 5, 6, 7, 8, 9, 10, 11, 12, 13, 14, 15, 16, 17, 18, 19, 20, 20 or more pn-hPSC cell lines. In various embodiments, the library includes pn-hPSC cell lines with HLA serotypes immunocompatible with 5%, 10%, 20%, 30%, 40%, 50%, 60%, 70%, 80%, 90%, 95% or more of an ethnic population. For example, the HLA haplotype A*01, B*08. DRB1*03 is present at a frequency of over 5% in Caucasian populations. In other embodiments, the HLA-serotypes include allelic variants of HLA-A, HLA-B, HLA-DP, HLA-DM, HLA-DOA, HLA-DOB, HLA-DQ, and HLA-DR In other embodiments, the HLA-serotypes include allelic variants of HLA-A, HLA-B, and HLA-DR. For example, this includes HLA-A serotypes A1-A3, A9-A11, A23-A26, A28, A29, A30-34, A36, A43, A66, A68, A69, A74 and A80, HLA-B serotypes B5, B7, B8, B12, B13, B14, B15, B16, B17, B18, B21, B22, B27, B35, B37-B72, B75-B78, B81, B*82 B*83, HLA-C serotypes CW01-CW08. Major histocompatibility complex II (MHCII) include HLA-DP serotypes DPA1 and DPB1, HLA-DM, HLA-DOA, HLA-DOB, HLA-DQ serotypes DQ2-DQ9, HLA-DR serotypes DR1-D18.

In other embodiments, the library includes pn-hPSC cell lines, each of which is hemizygous or homozygous for at least one MHC allele present in a human population, wherein each member of said library of pn-hPSCs is hemizygous or homozygous for a different set of MHC alleles relative to the remaining members of the library. In further embodiments, the library of human embryonic stem cells comprises pn-hPSC's that are hemizygous or homozygous for all MHC alleles present in a human population. The described methods can be applied to generate a library of pn-hPSCs each of which is hemizygous or homozygous for at least one MHC allele present in a human population, wherein each member of said library of pn-hPSCs is hemizygous or homozygous for a different set of MHC alleles relative to the remaining members of the library. In further embodiments, these methods generate a library of pn-hPSCs that are hemizygous or homozygous for all MHC alleles present in a human population. Thus, this invention also provides a library of pn-hPSCs made by such methods.

Also described herein is a specifically contoured enucleation pipette, described as a "knife pipette". In one embodiment, the contoured enucleation pipette is prepared by pulling a sterile glass tube, which is then broken, melted into a blunted round bead end by fire-polishing, sharpened by contacting and re-pulling on a microforge. In various embodiments, the contoured enucleation pipette includes: 1) a solid pointed fine tip, 2) slightly rounded contour edge resulting from the pulled bead end, and 3) larger hollow tube body of approximately 50 um in diameter.

In various embodiments, any of the enucleation methods described herein can be practiced using the contoured eucleation pipette. For example, enculeation may be performed by holding an oocyte with a micropipette on one side, advancing the fine tip of the contoured eucleation pipette against a lateral edge of the oocyte, with penetration followed by oocyte manipulation via the rounded pulled bead end for pinching of the penetrated fissure and positioning of the polar body near the edge of the fissure, the polar body positioned near the fissure can then be squeezed out for extraction.

Described herein is a method for inducing release of and/or isolating human oocytes. In one embodiment, the released and/or isolated human oocytes are used for parthenogenesis. In another embodiment, the released and/or isolated human oocytes are used for somatic nuclear transfer (SCNT). In various embodiments, ovarian hyperstimulation is used to stimulate the production of multiple eggs by follicle stimulating hormone (FSH) analogs and preventing spontaneous ovulation by the use of gonadotropin-releasing hormone (GnRH) agonists/antagonists or other leutenizing hormone (LH) surge inhibitors. In another embodiment, the method includes follicle maturation tracking with 2D or 3D ultrasound and estradiol level monitoring.

In another embodiment, the method uses in vivo maturation of human oocytes within the ovarian follicle, using human chorionic gonadotropin (hCG) or hCG analogs. In one embodiment, the final ovarian follicle maturation takes place within the oocyte donor by hCG stimulation. In another embodiment, coasting reduces the risk of OHSS (ovarian hyperstimulation syndrome). In another embodiment, the method includes the use of 2D or 3D ultrasound for antral follicle counting.

In another embodiment, the method includes the isolation of human ooctyes without hCG stimulation and completing oocyte maturation in vitro, using real-time non-UV light based monitoring for first polar body extrusion (1PBE). In another embodiment, the method includes determining 1PBE rate, to quantitate the rate of oocyte maturation. In another embodiment, the method includes improving the rate of oocyte maturation to enhance blastocyst formation rate with parthenogenesis and/or SCNT, thereby improving the efficiency of human pluripotent stem cell (hPSC) production.

In another embodiment, the method includes use of transvaginal ovum retrieval for harvesting multiple mature oocytes by suction-assisted, ultrasound-guided needle aspiration of the ovarian follicle, using a transvaginal approach with IV sedation, general, or paracervical block anesthesia. In another embodiment, local anesthesia is not used.

EXAMPLES

The following examples are provided to better illustrate the claimed invention and are not to be interpreted as limiting the scope of the subject matter. To the extent that specific materials are mentioned, it is merely for purposes of illustration and is not intended to limit the invention. One skilled in the art may develop equivalent means, compositions or reactants without the exercise of inventive capacity and without departing from the scope of the present invention.

Example 1

General Procedures Related to Parthenogenesis

The critical procedures for parthenogenesis involve 1) preparation of human MII stage oocytes 2) activation of oocytes 3) generation of parthenotes 4) further in vitro culturing up to blastocyst stage and 5) derivation of human pluripotent stem cells (hPSC) from cultured blastocysts. Cells derived via this process are parthenote-derived human pluripotent stem cells (pn-hPSCs).

Example 2

General Procedures Related to SCNT

Somatic cell nuclear transfer (SCNT) involves overlapping techniques with parthenogenesis, although the key differences involve the transfer of donor nucleus to recipient oocyte and embryo reconstruction. More specifically, SCNT includes 1) preparation of nuclear donor cells, 2) preparation of human MII stage oocytes, 3) enucleation of oocytes, 4) somatic cell nuclear transfer to the enucleated oocytes, 5) activation of the somatic cell nuclear transferred (reconstructed) eggs, 6) culture of the reconstructed eggs in vitro up to blastocyst stage, and 7) derivation of embryonic stem cell lines from those embryos. Cells derived via this process are somatic cell nuclear transfer human pluripotent stem cells (NT-hPSCs).

Example 3

Preparation of Nuclear Donor Cell Lines Using Adult Fibroblast Cells

Donor patients' fibroblasts can be grown from skin biopsies with individual cells retrieved from the monolayer by trypsinization, or similar process. Nuclei can then be obtained from adult fibroblast cells, using the following example protocol.
1. Obtain skin or other tissue biopsy under local anesthesia (50 mg, 0.5×0.5 cm).
2. Wash tissue fragment twice in PBS.
3. Mechanically mince tissue with a surgical blade on a 100-mm culture dish and carefully remove PBS from minced tissue.
4. Re-suspend tissue pellet in a 4.5 ml DMEM supplemented with 10% FBS, 1% non-essential amino acids and 10 ug/ml penicillin-streptomycin solution, and 500 ul (2000 unit/ml) of collagenase type II (Life Technologies).
5. Place into incubator overnight.
6. Centrifuge at 300×G for 3 min, and re-suspend cell pellet in DMEM with 10% FBS.
7. Seed cells into a 60-mm culture dish and subsequently culture until confluent in DMEM with 10% FBS, 1% non-essential amino acids and 10 ug/mL penicillin-streptomycin solution at 37° C. at 5% CO2 and 95% in air.
8. Once the cells reach to 80% confluency, cryopreserve ½ of initial outgrowths, and split the remaining cells into 1:3 ratios, and culture them in the above mentioned medium. Repeat this procedure 2 more times to obtain enough cells for SCNT and future genotyping analysis. At the end of the cell culture, cryopreserve all of the remaining cells in FBS supplemented with 10% DMSO. Either freshly prepared cells or cryopreserved cells can be used as nuclear donors.

Example 4

Preparation of Nuclear Donor Cell Lines Using Cumulus Cells

For SCNT, donor nuclei will also be obtained from the cumulus cells of the donor as described below, or from other tissues including commercially available adult stem cells. Nuclei can then be obtained from cumulus cells, using the following example protocol.
1. Approximately one-half of the cell preparation from each individual is used for SCNT as nuclear donor, and the rest will be snap-frozen for genotyping.
2. Collect the cumulus cells during the denudation process into a 1.5 ml micro-centrifuge tube. Add Hepes-HTF up to 1.5 ml and centrifuge for 1 min at 1200 rpm.
3. Decant the supernatant, leaving only the cell pellet, add and mix the pellet with 100 ul of 4% PVP solution (PVP, MW 36000, Calbiochem, and San Diego, Calif.). These cells are ready for nuclear injection.

Example 5

Ovarian Stimulation Protocol and Oocyte Retrieval

Patients are pre-treated with low-dose oral contraceptives for 7-14 days. Following withdrawal from the oral contraceptives, gonadotropins (Gonal-F or Follistim) and (micro-dose Lupronor hCG or Menopur) will be administered. Starting dosage is based on patient characteristics (age, day 3 FSH, APC) and determined by the individual physician. Transvaginal ultrasound assessment of follicular growth and endometrial thickness commences on day 6, and serum E2 levels are measured at each one of eight sequential clinic visits. Thereafter, based on the ultrasonographic findings and serum E2 levels, one can adjust the frequency of monitoring and the amount of gonadotropins.

The day of hCG trigger (and thus total days of stimulation) will be based on follicle size and number, in addition to the serum E2 level. The dose of Lupron or hCG can be administrated at 250 μg dosage. Egg retrieval is performed 36 hours after the administration of hCG. The patient will restart oral contraceptives the day following her egg retrieval.

Example 6

Ovarian Stimulation, Specifically

Egg retrieval can be performed using the following example procedure.
1. Treat healthy female donors between the ages of 20-34 with recombinant follicular stimulating hormone (FSH) (Follistim, 100-150 units, Schering-Plough) after low dose oral contraceptive for 7-14 days, and micro-dose recombinant LH (Lupron or hCG, 250 ug) EMD Serono starting from day 1.
2. The FSH usually starts with 100-150 units and can be adjusted as folliculogenesis proceeds.
3. Give a single dose of Lupron or hCG (250 ug) when two leading follicles reach 18 mm in diameter to induce oocyte maturation.

Example 7

Collecting Oocytes

Collection of oocytes can be performed using the following example procedure.
1. Collect cumulus mass from aspirated follicular fluid in 50×9 mm petri dish with Quinn's Advantage Fertilization Medium (SAGE catalogue #1021).
2. Treat the collected cumulus mass with Hyaluronidase (40 U/ml) for about 2-3 minutes in 37° C. 5% CO2 humidified incubator until the cumulus cells disperse.
3. Use the Stripper Tips (Mid-Atlantic Diagnostic, #MXL3-100 u) to remove any residual granulosa cells.
4. Wash oocytes twice with Quinn's Fertilization medium.
5. Prepare 50 ul drop covered with mineral oil in Willco-Dish glass petri dish (50×9 mm).

Example 8

Oocyte Retrieval and Preparation

Oocyte retrieval and preparation will be performed in a laboratory illuminated with green light (wavelength >500 nm).
1. Sedate patients with Midazolam 5-7.5 mg (Versed, Roche, and Nutley. N.J., USA) and Fentanyl 50-75 ug (Abbott Pharmaceutical, Abbott Park, Ill. USA) 36 hrs post Lupron or hCG injection and oocytes are then retrieved using ultrasound guidance as previously described.

2. Wash and incubate the freshly-isolated cumulus-oocyte cell complexes (COCs) in IVF medium (Quinn's IVF medium, SAGE Biopharma, Bedminster, N.J.) for 2 hrs in a humidified incubator with 5% CO2.
3. Treat COCs with hyaluronidase (100 IU/ml, Sigma, St. Louis, Mo. USA) for 2 min and denude with a small bore micropipette (150 um diameter). Denuded oocytes with a single first polar body are classified as metaphase II (MII) and used for SCNT.

Example 9

Somatic Cell Nuclear Transfer

Metaphase II (MII) spindles are visualized for enucleation using the Oosight™ spindle imaging system (Cambridge Research & Instrumentation, Woburn, Mass. USA). This approach avoids Hoechst staining and UV light exposure. Oocytes will be pre-incubated in Quinn's Advantage® medium with HEPES (Cooper Surgical) containing 0.5 ug/ml cytochalasin B for 5 minutes.

Enucleation of oocytes will be performed using a Piezo Impact drill (PrimeTech, Tokyo, Japan) with an enucleation pipette (20 um in diameters). The removal of metaphase spindles will be confirmed by the presence of a bright oval-shaped nuclei complex in the manipulation pipette. Donor human fibroblast cells (or equivalent other type of cells) will be prepared. Those nuclear donor cells are fused or injected using the same systems used for enucleation. All procedures are performed without direct contact with fluorescent light.

Example 10

Somatic Cell Nuclear Transfer I: Direct Injection Method

A) Enucleation of Oocytes
1. A batch of oocytes (10) possessing visible first polar body are moved to pre-equilibrated culture medium containing cytochalasin B (5 ug/ml).
2. Move the oocytes into small drop of enucleation medium (Hepes-HTF+5 ug/ml cytochalasin B, Cooper Surgical) prepared on a micromanipulation dish.
3. Load the dish with oocytes onto the micromanipulation system with heated stage.
4. Hold the oocytes with the metaphase plate between 2 o'clock and 4 o'clock positions using Oosight™ imaging system (Cambridge Research & Instrumentation. Woburn, Mass. USA) to visualize spindle).
5. Place enucleation pipette onto the surface of zona pellucida (3 o'clock position) and deliver the PIEZO (PrimeTech, Tokyo, Japan) pulse to make a hole through the zona.
6. Advance enucleation pipette (under very slight positive pressure) into the impacted area just after the zona is pierced.
7. Remove chromosome-spindle complex by suction along with a small volume of cytoplasm.
8. Repeat procedure for all oocytes.
9. Wash the enucleated oocytes thoroughly in a culture medium (Cleavage Medium, Cooper Surgical) to remove a trace of the cytochalasin B, and culture in fresh culture medium for 10-15 min before nuclear injection.

B) Nuclear Transfer
Prior to NT, retrieve individual fibroblast cells (or other type of nuclear donor cells) from the monolayer by trypsinization with 0.25% (v/v) trypsin-EDTA (Life Technologies) for 30 sec at 37° C. and subsequently used for NT. Gently mix the donor fibroblast cells into a drop with Quinn's fertilization medium. Donor nucleus may be from denuded cells, and/or cells subjected to epigenetic modification prior to nuclear transfer.
1. The nuclear donor cells (cumulus cells, skin fibroblast cells) are washed in Hepes-HTF (SAGE Biopharma), centrifuged, and reconstituted in 4% PVP solution.
2. The nuclei are isolated by applying several pulses and vigorous pippetting using the PIEZO system.
3. Inject the nuclei into the ooplasm of the enucleated oocyte using the PIEZO system.
4. Remove the injected oocytes to fresh culture medium; incubate for 30 min before the protein injection.
5. Remove the injected oocyte to a manipulation dish to inject a mixture of centrosome core proteins (human Aurora B kinase+hSET+NuMA). All proteins are available in CBI's labs.
6. Inject the proteins, approximately 4 pL per egg.
7. Remove and incubate the injected oocytes in the culture medium for 30 min before activation.

C) Activation of the Reconstructed Egg
1. Treat the NT eggs in an activation medium (5 uM ionomycin) for 5 min at 37° C. and wash them thoroughly in cleavage medium.
2. Re-treat the eggs in post-activation medium (2 mM 6-DMAP in Cleavage medium with 5 nM trichostatin A (TSA)) for 4 hrs.
3. Wash the activated eggs in 6-DMAP free medium and incubate in culture medium containing 5 nM TSA (Cleavage medium) for 6 hrs before transferring them to the normal culture medium.
4. Culture the activated eggs in SAGE cleavage medium for the first 2 days and in SAGE Blastocyst medium for next 3 days.

Example 11

Improved Techniques for Enucleation of Oocytes

Some leading techniques for enucleation of oocytes include the aforementioned Piezo electric drill piercing and suction, or hollow needle point puncture and extrusion. Another well-known technique includes the "chopstick" method of using large bore suction holding pipette and lateral edge puncture of the oocyte via a fine tip pipette and shearing of a part of the cell membrane. Via the shearing motion, the fine tip pipette allows extraction of genetic material through sequestration of the polar body between the puncture tear and fine tip pipette for extraction. A disadvantage of these techniques is the mechanical stress placed on the manipulated oocyte, which may lead to diminished cell viability and inefficient cell line generation.

Described herein is an improved enucleation technique using a specially designed enucleation pipette. This "knife pipette" can be prepared by pulling a sterile glass tube, which is then broken and melted into a blunted round bead end by fire-polishing. The blunted round bead end of pipette was sharpened by contacting and re-pulling on a microforge. This process leads to formation of "knife pipette" including multiple features: 1) a solid pointed fine tip, 2) slightly rounded contour edge resulting from the pulled bead end, and 3) larger hollow tube body of approximately 50 um in diameter. In combination with a fire-polished holding pipette (outer diameter: 120-150 um; inner diameter: 20-30 um) that is used to hold the human mature oocytes stationary, superior micromanipulation for enucleation can be achieved.

For example, as shown in FIG. 1, the contours of the "knife pipette" allow effective penetration of the zona pellucida via the (A) solid pointed fine tip, when the tip is advanced against (B) a lateral edge of a cell held stationary by holding pipette. (C) Penetration is followed by oocyte manipulation via the rounded pulled bead end for "pinching" of the fissure and (D) positioning of the polar body near the edge of the fissure. With the larger hollow tube body providing a bulk structure for the user to more easily grasp the knife pipette, (E) the polar body positioned near the fissure can then be (F) squeezed out for extraction. The combination of these features together in a single enucleation pipette allows each step to be performed quickly with a single device, thereby reducing physical manipulation of the oocyte and reducing the size of cell membrane fissures. Enucleation can then be confirmed by Oosight™ imaging system (poloscopic microscopy).

Example 12

Somatic Cell Nuclear Transfer II: Somatic Cell Fusion Method

A) Enucleation of Oocytes, as Described.
B) Transfer of Somatic Cells in Perivitellin Spaces
  1. Pick up 3-4 donor cells in a line in an injection pipette (12 um in diameter). During this process, care should be taken not to disrupt the plasma membrane.
  2. Hold oocyte with holding pipette.
  3. Place the injection pipette onto surface of zona pellucida and apply the PIEZO pulse to make a hole through the zona.
  4. Advance the injection pipette with donor cells into the oocyte without breaking the oolema and insert gently one nuclear donor cell in the perivitelline space in a way that it contacts the oolema closely.
  5. Gently withdraw the pipette, relatively rapidly first, and then slowly.
  6. Complete this procedure for entire group of oocytes and return them into an incubator.
C) Oocyte-Somatic Cell Fusion
  Electrofusion will be performed in electrofusion buffer (0.3M D-sorbitol, 0.1 mM calcium acetate, 0.5 mM magnesium acetate, 0.1 mM HEPES, 0.5 mg/ml polyvinylpyrrolidone, 50 uM D-myo-2,4,S, inositol triphosphate) with a BTX 200 Electro Cell Manipulator™ (BTX Harvard Apparatus, Holliston, Mass. USA) using a 0.5 mm electrofusion chamber.
  1. Align 3-4 oocyte-somatic cell couplets between 2 wires of an electofusion chamber covered with the electrofusion buffer.
  2. Apply a DC pulse of 160 Kev/Cm for 5 μsec. Or alternatively, longer period such as 20 μsec, may be applied.
  3. Wash the reconstructed oocytes thoroughly in embryo culture medium and culture them in a 4-well dish (10 cells/well) in Global medium (0.3% human serum albumin+Global medium).
  4. Check the fusion in 30 min after the initial pulse. Repeat one more time for the unfused couplets.

D) Activation of the Reconstructed Egg
  Activate the reconstructed oocytes using the same method in Somatic Cell Nuclear Transfer I.

Example 13

Sendai Virus-Based Oocyte-Somatic Cell Fusion

An improved technique for achieving oocyte-somatic cell fusion is described herein, which relies on application of recombinant protein envelope from the negative sense, single-stranded RNA Sendai virus (SeV). The SeV virus is known for its capacity for fusion of eukayotic cells, and recombinant SeV surface envelope protein (SeV-E) free of any genetic materials can be applied without risk of infective or proliferative capacity.

Applying SeV for oocyte-somatic cell fusion, begins with preparing freeze-dried SeV-E in suspension buffer according to manufacturer protocol (GenomONE-CF EX, Ishihara Sangyo Kaisha, Cat #ISK-CF001-EX). SeV-E in suspension buffer is then added to previously diluted 20× cell fusion buffer. SeV-E in combined mixture buffer is then added via microdroplet addition positioned between a pipette tip containing a donor nucleus somatic cell and a recipient enucleated oocyte. The cell may be from denuded cells, and/or cells subjected to epigenetic modification prior to nuclear transfer. Coating of the cell membrane surfaces of the donor nucleus somatic cell and a recipient enucleated oocyte with SeV-E in mixture buffer via microdroplets allows somatic cell fusion to occur without use of electrofusion. This reduction in physical and electrophysiological stress on the recipient oocyte improves cell viability and efficient cell line generation.

Example 14

Improved Techniques Using Sendai Virus-Based Somatic Cell Fusion

A) Enucleation of Oocytes
  Remove the MII stage egg spindle complex using the "knife pipette" method described in Example 11 and elsewhere (FIG. 1). The Oosight™ (Spindle view) was used throughout this procedures to eliminate oocyte's exposure to UV light. It is important to remove the 1st polar body in every oocytes, otherwise, it can be fused with oocyte during the fusion process.
B) Transfer of Somatic Cells in Perivitellin Spaces
  1. Pick up 3-4 donor cells in a line in an injection pipette (12 um in diameter). During this process, care should be taken not to disrupt the plasma membrane.
  2. Expel the donor cells in a small drop of the Sendai virus envelop protein and pick up them again with short distance (4-5 cell length) between each cell.
  3. Hold oocyte with holding pipette.
  4. Advance the injection pipette with donor cells into the oocyte without breaking the oolema and insert gently one nuclear donor cell in the perivitelline space in a way that it contacts the oolema closely.
  5. Gently withdraw the pipette without disturbing oolema and donor cell contact.
  6. Complete this procedure for entire group of oocytes and return them into an incubator.
  7. Check the fusion 10 min after the donor cell insertion. The fusion process occurs relatively rapidly, thus repeat above procedures if the fusion does not occur within 15 min after cell insertion.

D) Activation and Culture of the Reconstructed Egg
1. Treat the NT eggs in an activation medium (5 uM ionomycin) for 5 min at 37° C. and wash them thoroughly in cleavage medium.
2. Re-treat the eggs in post-activation medium (2 mM 6-DMAP in Cleavage medium) for 4 hrs at 37° C. in 5% CO2/5% N2/90% N2 atmosphere.

Example 15

Improved Techniques for Reconstructed Oocyte Activation

At present, various reports of NT suggest activation of reconstructed nuclear transfer oocytes (embryos) at the 8-cell stage as a limiting step preventing efficient cell line generation, as oocyte development switches from maternal RNA-based transcription to host genome activation. Up to as few as 2% of reconstructed oocytes cross this critical threshold, but it is presently unknown what biological factors may enhance genome activation.

Described herein is the hereto unknown discovery that sperm factors, such as factors present in sperm head and particularly, the mid-connecting piece, and sperm tail, can be applied to improve genome activation of reconstructed oocytes during NT. Without being bound by any particular theory, centrioles, important complexes required for mitotic spindle formation are absent in MII stage oocytes. The absence of centrioles in reconstructed oocytes may explain a key limitation on genomic activation during NT. Yet these proteins are known to be located within the connecting piece between the sperm head and mid-connecting piece of human sperm and addition of sperm factors during the activation process can improve genomic activation by providing the biological machinery necessary for mitotic divisional.

Example 16

Preparation of Sperm Factor for Oocyte Activation

More specifically, sperm factors may be obtained by isolating cell proteins present inside or outside of sperm cells by treating ejaculated sperm with detergents and mechanical blending, then the whole sperm cell extracts are treated with DNAase I and RNAase to eliminate any genetic material contaminations. The final step is concentrating the crude extract by washing in buffer and centrifugation (20,000 g for 2 hours).
1. Collect fresh ejaculated human sperm, and centrifuge at 900 g for 10 min to remove seminal plasma.
2. Resuspend the pellet in Sperm-TALP containing 5 mg/mL bovine serum albumin, and centrifuged at the same setting.
3. Remove supernatant and resuspend the sperm pellet to a final concentration of $20 \times 10^8$ sperm/mL in nuclear isolation medium ((NIM: 125 mM KCl, 2.6 mM NaCl, 7.8 mM Na2HPO4, 1.4 mM KH2PO4, 3.0 mM EDTA disodium salt; pH 7.45 (Kuretake et al., 1996)) and centrifuged to remove Sperm-TALP.
4. Resuspend the pellet to the same volume with NIM containing 1 mM dithiothreitol, 100 mM leupeptin, 100 mM antipain, and 100 mg=mL soybean trypsin inhibitor.
5. Then the suspension is subjected to four cycles of freezing (5 min per cycle in liquid N2) and thawing (5 min per cycle at 15° C.), then sperm were pelleted at 20,000× for 50 min at 2° C.
6. The resulting supernatant is carefully removed, aliquoted, and kept at −80° C. until use.

The human sperm factors are then injected into the reconstructed eggs using any of the described injection methods. At about twenty-four hours later, oocytes are switched to cleavage medium. After an additional twenty-four hours, oocytes are transferred to G2 culture medium. Using this approach, the inventor can achieve up to 40-80% success rate of successful reconstructed oocyte activation, virtually eliminating this previously onerous obstacle for successful NT.

Example 17

Improved Techniques for Establishing Pluripotent Stem Cell Line

While general techniques for establishing pluripotent stem cells from cultured blastocysts have advanced significantly in the past decade, successful application to NT has yet to be achieved. Without being bound by any particular theory, it appears that at least one significant limitation is the epigenetic state of donor nucleus. In particular, the methylation state of an adult nucleus, or other epigenetic factor, may prevent effective reprogramming when transferred into the embryonic development processes of a recipient oocyte. In this regard, modification of the donor cell, and its nucleus, towards an embryonic methylation state, prior to NT may present an opportunity to sidestep the obstacle in generating of NT-hPSC cell lines.

Two approaches are suggested. The first approach includes use of reprogramming factors delivered to nuclear donor cells prior to NT. Examples of reprogramming factors include octamer binding transcription factor-4 (Oct-4), sex determining region Y-box-2 (Sox-2), Kruppel-like factor 4 (KLF-4), c-myc, and nanog. Such reprogramming factors have been previously utilized in generation of induced pluripotent stem cells (iPSCs) from adult somatic cells, thereby demonstrating their potential to alter nuclear state towards more primitive development states. Other more recently described reprogramming factors, such as orphan nuclear receptor estrogen related receptor β (Esrrb), can similarly be applied, as accessibility of reprogramming factors to the nucleus may enhance the efficiency of reprogramming effects in target cells. Along the same lines, transactivation domains of other early embryonic transcription factors, such as MyoD, can be fused with reprogramming factors (e.g., Oct4-MyoD fusion protein) to achieve the same effect.

The second approach is to rely on methylation-altering agents that change the methylation state of donor nuclei prior to NT. Using this approach, methyltransferases such as protein arginine methyl-transferase (PRMT1) and coactivator-associated arginine methyltransferase 1 (CARM1/PRMT4), co-activator associated proteins known to be involved in changing histone methylation, can be delivered to donor nuclear donor cells prior to NT. Application of these methylation-altering proteins provides a mechanism for generating the epigenetic modifications that allow NT-hPSC cell line generation.

As described herein, the inventors have successfully applied two recombinant proteins, Esrrb and CARM1, conjugated with 7× arginine (7R)-cell-penetrating peptides (CPPs), to reproducibly generate NT-hPSC at nearly 30% efficiency from activated, reconstructed oocytes. Molecular DNA fingerprinting using human short tandem-repeat (STR) probes confirmed the resulting NT-hPSC cell lines as possessing characteristics identical to, or nearly identical to the nuclear donor. In various applications, it was advantageous to apply culturing conditions known to support pluripotency. This includes, for example, application of 3i medium (Neuro basal medium 50%, DMEM/F-12 50%, N2 supplement 1/200 v/v, B27 supplement 1/100 v/v, 100 mM L-glutamine 1/100 v/v, 0.1M ß-ME 1/1000 v/v, SU5402 (FGFR inhibitor) 2 µM, PD184352 (ERK cascade inhibitor) 0.8 µM, CHIR99021 (GSK3 inhibitor) 3 µM) or modified 3i medium (including PD0325901 (MAPK inhibitor) 0.4 µM).

Without being bound by any particular theory, it is suggested that the application of Esrrb and CARM1 exploit interactions with key transcription factors involved in establishing and maintaining pluripotency. For example, Esrrb has an important role on the maintenance of the undifferentiated state and regulates the expression of Oct-4 and nanog genes as a transcription factor in the stem cells and embryos. CARM1 methylates H3 arginine residues 17 (H3R17) and R26 was known to control expression of many genes via regulation of various transcription factors. It was reported that treatment of CPP-Esrrb and CPP-CARM1 upregulated the expression of Oct-4, Sox-2 and nanog of adult stem cells. In each case, penetration through the cell membrane, and nuclear entry after simple addition into culture medium appeared to contribute to pluripotent marker expression. In addition, CPP-Esrrb and CPP-CARM1 in the culture medium may increase the expression of Oct4. In turn, these interactions appear to aid the cell number of blastocysts derived from vitrified/warmed mouse embryos and cloned human embryos.

This breakthrough achievement in NT-hPSC cell line generation, previously unachieved by others, demonstrates proof-of concept that modification of donor nucleus prior to NT is a key step for successful NT-hPSC cell line generation using reprogramming factors and/or methylation-altering agents.

Example 18

Results Using Improved Techniques for Establishing Pluripotent Stem Cell Line

A) Enucleation of Oocytes
Remove the MII stage egg spindle complex using the "knife pipette" method described in Examples 11, 14 and elsewhere (FIG. 1)
B) Transfer of Somatic Cells in Perivitellin Spaces
Transfer somatic cell donor nucleus as described in Example 14 and elsewhere.
D) Activation and Culture of the Reconstructed Egg
  1. Treat the NT eggs in an activation medium (5 uM ionomycin) for 5 min at 37° C. and wash them thoroughly in cleavage medium.
  2. Re-treat the eggs in post-activation medium (2 mM 6-DMAP in Cleavage medium) for 4 hrs at 37° C. in 5% CO2/5% N2/90% N2 atmosphere.
  3. Wash the activated eggs in 6-DMAP free medium and culture the activated eggs in SAGE cleavage medium for the first 2 days and in G2 medium supplemented with CARM1 and/or Esrrb, each at 2 µg/ml) for next 3 days.
E) Pluripotent Stem Cell Derivation
  1. Treat the cultured blastocyst acidic Tyrode's solution (pH 2.0) for a few seconds to remove a zona pellucida (ZP). After the ZP removal, wash the embryos vigorously in Hepes-HTF medium to remove any trace of the Tyrode's solution.
  2. Isolate the inner cell mass (ICM) using the Laser-assisted blastocyst dissection system (Hamilton-Thorne Inc.) if the ICM is visible. Discard the remaining part (trophoblast) of blastocyst to make sure that the blastocysts are no longer intact.
  3. Plate the ICM on top of the MEFs which are prepared one day before the plating. However, plate whole embryos if the cloned blstocysts have indistinguishable ICM. The hPSC derivation medium is composed of knockout-DMEM supplemented with serum replacement (5% SR, Invitrogen), FBS (10%, Hyclone), plasmamate (5%), bFGF (32 ng/ml), and human LIF (2000 units/ml, Sigma-Aldrich).
  4. Culture the ICM in the same medium for 3 days without any change.
  5. Replace approximately ⅓ of the medium on day 4.
  6. Replace ½ of the medium every other day from day 6.
  7. The initial outgrowths are seen within 7 days after plating.
  8. Expand and cryopreserve the colonies before day 12

As described, using conventional techniques, only up to 2% of reconstructed oocytes cross the 8-cell threshold, thereby effectively limiting the generation of NT-hPSC through failure to induce blastocyst formation. However, using the techniques described herein, the inventors have removed this obstacle using methylation altering agents, such as CARM and Esrrb. As shown in Table 1, non-treated reconstructed oocytes did not progress to early blastocyst formation in 16 samples. Consistent with existing reports, the vast majority of such oocytes fail developed beyond 4-cell and 8-cell stages. By contrast, 9 CARM-treated reconstructed oocytes were able to reach early blastocyst stage from 47 samples. Remarkably, nearly ⅔ of these CARM-treated reconstructed oocytes were further capable of forming expanding blastocysts. Similarly, 3 Esrrb-treated reconstructed oocytes were able to form early blastocysts from 6 samples, although none of these reconstructed oocytes formed expanding blastocysts. In either case, CARM and/or Esrrb treatment clearly permitted development of reconstructed oocytes beyond the 8-cell stage compared to controls, thereby eliminating a previously insurmountable barrier for generation of NT-hPSC cells. (Table 1)

TABLE 1

The effects of CARM and Esrrb proteins on SCNT embryo culture

| Treatments | No. oocyte | 2-cell | 4-cell | 8-cell | morular | Early Blast | Exp. Blast |
|---|---|---|---|---|---|---|---|
| Non-treat | 16 | 15 | 14 | 3 | 1 | 0 | 0 |
| CARM | 47 | 43 | 37 | 28 | 16 | 9 | 6 |
| Esrrb | 6 | 6 | 6 | 6 | 3 | 3 | 0 |

Demonstrating the capacity of such cells to form blastocysts by which NT-hPSCs can be isolated and culture, reconstructed ooytes were further cultured, plated as described on mouse embryonic feeders (MEF), wherein initial out growth was observed. Following additional culturing, inner cell mass (ICM) cells were separated from trophectoderm, and capable or surviving initial passage.

Figure 2:
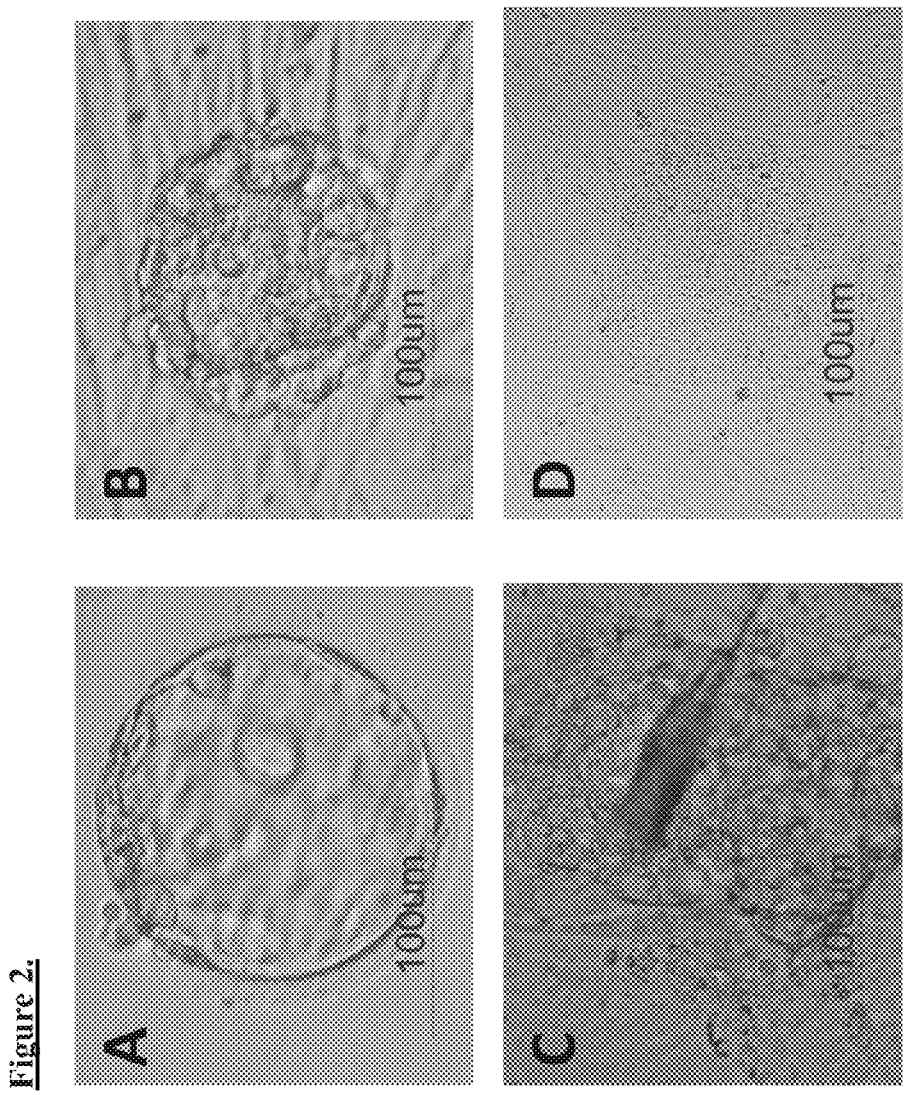
FIG. 2. Derivation of NT-PSC. (A) somatic cell nuclear transferred blatocyst (B) plated embryo after the zona pellucida removal (C) initial outgrowth of the NT-embryos (D) Embryonic cell like colonies formed after 3 passages.

This is shown in FIG. 2, wherein (A) somatic cell nuclear transferred blastocyst is shown, which was then (B) plated after removal of the zona pellucida removal. Such cells were capable of survival as (C) initial outgrowth of the NT-embryos was observed. Isolation of ICM cells resulted in (D) embryonic cell like colonies formed after 3 passage. In at least one instance of a CARM-treatment, cells isolated from blastocyst were capable of surviving more than 3 passages, thereby demonstrating successful generation of a NT-hPSC cell lines. (Table 2)

TABLE 2

The effect of CARM protein on NT-hPSC cell derivation

| Treatment | Plated | Initial outgrowth | Passage 1 | ≥3 Passages |
|---|---|---|---|---|
| CARM | 7 | 2 | 2 | 1 |
| Esrrb | 3 | 0 | 0 | 0 |

Example 19

Parthenogenesis of Oocytes

Parthenogenesis is a second distinct approach that could be used to generate hPSC cells. Production of hPSC cells through parthenogenesis, described herein as parthenote-derived hPSCs (pn-hPSCs) are genetically identical to the donor oocyte and provides a method for generating hPSC cells for any ova-producing woman. Additionally, because parthenogenesis involves no paternal contribution, the HLA complexity of pn-hPSCs is substantially reduced in comparison to hSPCs cells generated using any paternal contribution. The reduced HLA complexity of pn-hPSCs cells greatly reduce the tissue compatibility issues, as pn-hPSCs can be engineered for broad compatibility with substantial segments of the population, even in the absence of exact genetic tissue matching. For example, although there is a high degree of HLA polymorphism, that are only approximate 200 common HLA haplotypes in existence within the U.S. Caucasian population. It has been estimated that a panel of as few as ten HLA homozygous hPSC lines selected for common haplotypes could provide a complete HLA-A, HLA-B, and HLA-DR match for nearly 40% of UK recipients and a beneficial match for nearly 65%. This immunocompatibility with wide swaths of the population creates the possibility of hPSC cell banking as a renewable source of transplant material. Crucially, self-renewal capacity of hPSC lines within banks of stem cells with broad tissue compatibility would reduce the need for an ongoing supply of new oocytes.

Example 20

Variable Approaches to Parthenogenetic Activation: pn-hPSC Cell Line Characteristics Some MII stage eggs obtained via the above described procedures can be used to generate parthenogenetic embryonic cell lines. The intact oocytes are activated and cultured using the same procedures described in Somatic Cell Nuclear Transfer I for generation of pn-HPSCs.

It is important to consider that existing reports of human parthogenesis demonstrate that differences in oocyte activation and post-activation techniques has a direct impact on the genetic components defining immunological characteristics of resulting pn-hPSC cell lines. For example, two specific approaches are generation of heterozygous pn-hPSC that are totally HLA matched with oocyte donors, or homozygous pn-hPSC that are histocompatible with significant segments of the population. Whereas parthenogenesis reduces genetic variation in an pn-hPSC cell line via elimination of paternal contribution, homozygous hPSC generation further reduces genetic heterogeneity via generation of HLA haplotypes by eliminating one source of allelic variation, and providing cells histocompatible with a wider range of individuals.

Example 21

Parthenogenesis I: Generation of Heterozygous pn-hPSCs

As described, the general approach for oocyte activation is to mimic the calcium-altering effects ordinarily caused by sperm entry. As one example, heterozygous HLA pn-hPSC lines can be generated by application of ionomycin for oocyte activation, followed by addition of puromycin analog 6-DMAP (6-aimtheylamino-purine), which reversibly prevents spontaneous germinal vesicle breakdown by inhibiting the activation of histone H1 kinase.

The step-wise addition of ionomycin and 6-DMAP first initiates a calcium flux, leading to inhibition of protein phosphorylation, these processes induce pronuclear formation without completion of meiosis. Other approaches rely on electrical activation of oocytes, followed by addition of ionomycin, and 6-DMAP. However, common to these techniques is the addition of 6-DMAP to promote pronuclear formation, which prevents extrusion of the second polar body, and leads to generation of diploid cells. This ordinarily does not allow for the generation of homozygous hPSC cell lines due to the formation of chiasmata (paternal and maternal genome recombination) during early embryogenesis. Thus, after first meiosis, the remaining oocyte nucleus is heterozygous possessing both maternal and paternal genome.

More specifically, parthenogenesis of oocytes for generation of heterozygous pn-hPSC lines can be obtained via the following procedure:

A) Oocyte Retrieval and Preparation
1. Treat cumulus-oocyte cell complexes (COCs) with hyaluronidase (100 IU/ml, Sigma, St. Louis, Mo. USA) for 2 min and denude with a small bore micropipette (150 um diameter). Denuded oocytes with germinal vesicles (GVs) or missing the first polar body are not used. Denuded oocytes with a single first polar body are classified as metaphase II (MII) oocytes.
Alternatively, COCs may be treated with SynVitro Hyadase to remove cumulus cells, followed by incubation with IVF medium with Paraffin overlay for 30 mins B) Activation of Oocytes
1. Treat the MII oocytes in an activation medium (5 uM ionomycin) for 5 min at 37° C. and wash them thoroughly in cleavage medium.
2. Re-treat the eggs in post-activation medium (1-2 mM 6-DMAP in cleavage medium with 5 nM trichostatin A (TSA)) for 4 hrs.
3. Wash the activated eggs in 6-DMAP free medium and incubate in cleavage medium containing 5 nM TSA for 6 hrs before transferring them to the normal culture medium.
4. Culture the activated eggs in SAGE cleavage medium for the first 2 days and in SAGE Blastocyst medium for next 3 days.
Alternatively, activation can be performed in IVF medium with paraffin overlay by consecutive exposure to 5 uM ionomycin for 5 min, and 1-2 mM 6-DMAP for 4 hours, careful washing and culturing in fresh IVF medium with paraffin overlay, followed by culturing in cleavage medium the next day.

Example 22

Parthenogenesis II: Generation of Homozygous pn-hPSCs

By contrast, a direct approach for generation of HLA homozygous hPSC cell line is to generate such a line from a HLA homozygous oocyte donor, including one-pronuclear oocytes. However, a key disadvantage of this approach is the relative rarity of homozygous donors in the population. Alternatively, HLA homozygous hPSC cell lines can be obtained from heterozygous donors by methods by excluding 6-DMAP addition, to allow second polar body extrusion (2PBE).

This approach, relying upon initial addition of an activator, such Ca2+ ionophores, A23817 or ionomycin and later, puromycin or cycloheximide without cytocalasin B, permits extrusion of the second polar body, therefore resulting in haploid parthenotes with only half a set of metaphase II chromosomes. These haploid parthenotes can be cultured further into diploid blastocysts for formation of a homozygous genotype.

More specifically, parthenogenesis of oocytes for generation of homozygous pn-hPSC lines can be obtained via the following procedure:
A) Oocyte Retrieval and Preparation, as Described.
B) Activation of Oocytes
1. Treat the MII oocytes in an activation medium (5 uM A23187) for 5 min at 37° C. and wash them thoroughly in cleavage medium.
2. Re-treat the eggs in post-activation medium (10 ug/mL puromycin cleavage medium or cycloheximide without cytochalasin B) for 4 hrs.
3. Wash the activated eggs and incubate in cleavage medium for 24 hours or until they developed to 2 cell stage embryos. These 2 blastomeres are then electrofused by applying 160 mV electricity for 20 micro second in manitol or sobitol based fusion medium using a electric fusion machine (BTX 2000, Harvard Electric). Optionally, a single pulse may be applied, and this has been shown to be sufficient to fuse the blastomeres. The refused eggs are cultured 1 more day in SAGE cleavage medium and in SAGE Blastocyst medium for next 3 days.

Example 23

Generation of hPSC Cell Lines

Following the generation of a parthenote (via parthenogenesis), subsequent culturing leads to blastocyst formation, from which hPSCs can be obtained from the inner cell mass via separation of surrounding trophectodermal tissue.
1. Treat the cultured blastocyst with Pronase (0.5%, Sigma-Aldrich) or acidic Tyrode's solution (pH 2.0) for a few seconds to remove the zona pellucida (ZP). After the ZP removal, wash the embryos vigorously in Hepes-HTF medium to remove any trace of the Pronase or Tyrode's solution.
2. Isolate the inner cell mass (ICM) using the Laser-assisted blastocyst dissection system (Hamilton-Thorne Inc.). Discard the remaining part (trophoblast) of blastocyst to make sure that the blastocysts are no longer intact.
3. Plate the ICM on top of the MEFs which are prepared one day before the plating. The hPSC derivation medium is composed of knockout-DMEM supplemented with serum replacement (10% SR. Invitrogen), FBS (5% Hyclone), plasmamate (5%), bFGF (32 ng/ml), and human LIF (2000 units/ml, Sigma-Aldrich).
4. Culture the ICM in the same medium for 3 days without any change.
5. Replace approximately ⅓ of the medium on day 4.
6. Replace ½ of the medium every other day from day 6.
7. The initial outgrowths are seen within 7 days after plating.
8. Expand and cryopreserve the colonies before day 12

Example 24

Characterization of pn-hPSC and NT-hPSC Cell Lines

A variety of genomic, transcriptome, epigenetic, protein, and/or functional studies can be performed to characterize resultant pn-hPSC and NT-hPSC cell lines. In one example, hPSC pluripotency markers, can be measured at the transcript (e.g., microarray, qRT-PCR) or protein level (e.g., western blot, immunocytochemistry, 2-D gel). These pluripotent markers include alkaline phosphatase (AP), stage-specific embryonic antigen-4 (SSEA-4), SSEA-3, tumor rejection antigen 1-81 (Tra-1-81), Tra-1-60, octamer binding transcription factor-4 (Oct-4), sex determining region Y-box-2 (Sox-2), nanog, zinc finger protein-42 (Rex-1/Zfp-42), lefty A, teratocarcinoma-derived growth factor (Tdgf), telomeric repeating binding factor (Terf-1), and developmental pluripotency-associated gene 2 (Dppa-2), among others.

Additionally, DNA fingerprinting with human short tandem-repeat (STR) probes can be used for genomic analysis of pn-hPSC and NT-hPSC cell lines. In the case of pn-hPSC, the resulting cell line is identical, or nearly identical to, the oocyte donor. In the case of NT-hPSC, the resulting cell line possess characteristics identical to, or nearly identical to the nuclear donor. Another key issue in confirming the successful generation of NT-hPSCs is eliminating the possibility of enucleation failures and subsequent parthenogenetic activation. In other examples, genomic DNA can be analyzed using single nucleotide polymorphism (SNP) microarrays to determine genetic equivalency. In one example, heterozygosity of binary SNP markers has a maximal value of 0.5, and analysis can be performed on SNP markers with a heterozygosity greater than 0.375 (frequency greater than 0.25, but less than 0.75 in a population). In another example, intermarker distance, such as 0.1 cM, can be used to exclude SNP markers of tight linkage, as they provide less information on an individual basis.

In another example, epigenetic studies can be performed. For example, methylation can also be analyzed using genomic DNA applied to arrays following bisulfite treatment, allowing interrogation of CpG sites.

Ultimately, the key properties of hPSCs are pluripotent capacity to differentiate into somatic cells from all three embryonic germ layers: ectoderm, mesoderm, and endoderm, and self-renewal. As such, pluripotency can be evaluated via teratoma formation via intramuscular (IM) injection into appropriate animal models (e.g., SCID mice), or by embryoid body (EB) formation following culture in low adherence conditions. Moreover, self-renewal capacity can be observed by high proliferation and continuous propaga-

Example 25

MHC-HLA Matching

Major histocompatibility complex (MHC)-human leukocyte antigen (HLA) matching is crucial for immunological tolerance during organ donations. In the absence of MHC-HLA matching, immunosuppressive medicines are required. As the degree of immune rejection risk is a function of the degree of disparity between donor and recipient cell-surface antigen presenting proteins, evaluating MHC-HLA profiles of pn-hPSC and NT-hPSC cell lines generated by the various described methods is critical.

MHC class I and II HLA haplotypes are specific sets of HLA-A, HLA-B, HLA-DP, HLA-DM, HLA-DOA, HLA-DOB, HLA-DQ, and HLA-DR locus alleles inherited together from a parent. Although there is a high degree of HLA polymorphism, that are only approximate 200 common HLA haplotypes in existence within the U.S. Caucasian population.

This MHC-HLA matching provides additional evidence that parthenogenetic errors had not occurred in the generation of pn-hPSC cell lines. As related to NT-hPSC cell lines, it is important to verify successful nuclear transfer to exclude inadvertent parthenogenic activation. To establish each NT-hPSC cell line is not an accidentally created pn-hPSC cell line, NT-hPSCs are checked against the respective donor's for all HLA isotypes.

Example 26

MHC-HLA I and II Serotypes

In different examples, HLA genotyping can be performed by extracting genomic DNA from various donor sources, such as blood or cumulus cells, and analyzing allelic variation via PCR of allele-specific sequencing primers. Major histocompatibility complex I (MHCI) include HLA-A serotypes A1-A3, A9-A11. A23-A26, A28, A29, A30-34, A36, A43, A66, A68, A69, A74 and A80, HLA-B serotypes B5, B7, B8, B12, B13, B14, B15, B16, B17, B18, B21, B22, B27, B35, B37-B72, B75-B78, B81, B*82 B*83, HLA-C serotypes CW01-CW08. Major histocompatibility complex II (MHCII) include HLA-DP serotypes DPA1 and DPB1, HLA-DM, HLA-DOA, HLA-DOB, HLA-DQ serotypes DQ2-DQ9, HLA-DR serotypes DR1-D18.

Example 27

Banking of HLA Homozygous HLA Type ES Cell Lines

As mentioned earlier, even though there is a high degree of HLA polymorphism, there are only approximate 200 common HLA haplotypes in existence within the U.S. Caucasian population. It has been estimated that a panel of as few as ten HLA homozygous hPSC lines selected for common haplotypes could provide a complete HLA-A, HLA-B, and HLA-DR match for nearly 40% of UK recipients and a beneficial match for nearly 65%. This immunocompatibility with wide swaths of the population creates the possibility of hPSC cell banking as a renewable source of transplant material. Crucially, self-renewal capacity of hPSC lines within banks of stem cells with broad tissue compatibility would reduce the need for an ongoing supply of new oocytes.

A direct approach for generation of HLA homozygous hPSC cell line is to generate such a line using somatic cells obtained from a HLA homozygous donor. A key disadvantage of this approach, however, is the relative rarity of homozygous donors in the population. One strategy to overcome this disadvantage is screening banked cord blood cells. In most cases, the HLA types of given cord bloods are tested and recorded before cryopreservation thus by simple document screening, those HLA homozygous cord blood cells (in particular mononuclear cells, $CD34^+$) samples are easily found then can be sorted, obtained and used as nuclear transfer donor cells. Anywhere between 30-50 HLA homozygous cell lines are generated and banked as transplant materials.

All the nuclear transfer procedures and embryonic stem cell derivation procedures are as same as described in this application.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the methods of parthenogenesis, somatic cell nuclear transfer, preparing, isolating, or modifying cells used in the described parthenogenesis or somatic cell nuclear transfer techniques, derivation of pluripotent cell lines from the aforementioned techniques, treatment of diseases and/or conditions that relate to the teachings of the invention, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of generating a nuclear transfer human pluripotent stem cell (NT-hPSC) cell line, comprising:
   removing the nucleus of an oocyte by using a knife pipette;
   generating a nuclear transferred (NT) oocyte by adding a nucleus from a donor cell, wherein adding the nucleus from the donor cell comprises contact of Sendai virus, protein or extract thereof, with the donor cell;
   activating the NT oocyte by addition of ionomycin followed by further culturing in the presence of 6-DMAP;
   generating a blastocyst from the activated NT oocyte by culturing in the presence of CARM1; and
   isolating inner cell mass (ICM) cells from the blastocyst, wherein the ICM cells are capable of further culturing as a NT-hPSC cell line.

2. The method of claim 1, wherein the donor cell is a somatic cell.

3. The method of claim 1, wherein the method is performed in the absence of ultraviolet light.

4. The method of claim 1, wherein the ionomycin concentration is 5 µM.

5. The method of claim 1, wherein the 6-DMAP concentration is 2 mM.

6. The method of claim 1, wherein the CARM1 concentration is 2 µM.

* * * * *